US005759991A

United States Patent [19]
Tohdoh et al.

[11] Patent Number: 5,759,991
[45] Date of Patent: Jun. 2, 1998

[54] NEUROTROPHIC PEPTIDE DERIVATIVES

[75] Inventors: Naoki Tohdoh, Kobe; Shin-ichiro Tojo, Ashiya; Shin-ichi Kojima, Kobe; Yasuyuki Ueki, Sagamihara; Toshio Nishihara, Osaka; Nobuyuki Fukushima, Yokosuka; Tsunemasa Irie, Tokyo; Keiichi Ono, Sakai; Hideo Agui, Ikeda, all of Japan; Kosei Ojika, 18, Aza Miyashinki Miwa-cho, Ama-gun, Aichi-ken, Japan

[73] Assignees: Sumitomo Pharmaceutical Company, Limited., Osaka, Japan; Kosei Ojika, Ama-Gun, Japan; Masahiko Yamamoto, Nagoya, Japan

[21] Appl. No.: 403,378

[22] Filed: Feb. 27, 1995

Related U.S. Application Data

[63] Continuation-in-part of Ser. No. 873,764, Apr. 27, 1992, abandoned, and Ser. No. 758,043, Sep. 12, 1991, abandoned, which is a continuation-in-part of Ser. No. 501,217, Mar. 29, 1990, abandoned.

[30] Foreign Application Priority Data

Apr. 27, 1991 [JP] Japan ................................. 3-124688

[51] Int. Cl.⁶ .......................... A61K 38/08; C07K 7/06; C07K 14/435
[52] U.S. Cl. .................. 514/2; 514/15; 514/16; 514/17; 530/327; 530/329; 530/350; 530/402
[58] Field of Search ....................... 514/2, 12–19; 530/324–331, 350, 402

[56] References Cited

U.S. PATENT DOCUMENTS 4,699,875 10/1987 Appel .
4,701,407 10/1987 Appel .
4,849,408 7/1989 Sommermeyer et al. .

FOREIGN PATENT DOCUMENTS 0390602 10/1990 European Pat. Off. .

3-72499 9/1991 Japan .

OTHER PUBLICATIONS

Ojika et al., Proc. Natl. Acad. Sci., USA, vol. 81, pp. 2567–2571 (April 1984).

Lin et al., Science, Research Articles, vol. 246, pp. 1023–1025 (Nov. 24, 1989).

Leibrock et al., Letters to Nature, vol. 341, pp. 149–152 (Sep. 14, 1989).

Angeletti and Bradshaw, Proc. Nat. Acad. Sci., USA, vol. 68, No. 10, pp. 2417–2420 (Oct. 1971).

Bostwick, Appel, Perez–Polo, Brain Research, vol. 422, pp. 92–98 (1987).

David K. Grandy et al., "Purification, Cloning, and ... Chromatography", Molecular Endocrinology, vol. 4, No. 9, pp. 1370–1376 (1990).

Françoise Schoentgen et al., "Complete amino acid sequence ... cytosol", European Journal of Biochemistry, vol. 166, No. 2, pp. 333–338 (Jul. 1987).

R. Jones et al., "A 23–kDa protein from rat sperm plasma ... cytosolic protein", Bochimica et Biophysica Acta, vol. 1080, No. 1, Amsterdam, NL, pp. 78–82 (1991).

Takemasa Kamiya, "The Effects of Hippocampal Cholinergic Neurostimulating ... Culture", Journal of Nagoya City University Medical Society, vol. 42, No. 4, pp. 945–960 (1991).

Primary Examiner—Paula K. Hutzell
Assistant Examiner—Stephen Gucker
Attorney, Agent, or Firm—Sughrue, Mion, Zinn, Macpeak & Seas, PLLC

[57] ABSTRACT

The invention provides human- or rat-derived neurotrophic peptides and derivatives thereof, precursor peptides thereof, genes encoding the same, transformants containing recombinant expression vectors bearing the genes, and compositions comprising as an effective ingredient these neurotrophic peptides or derivatives thereof. The neurotrophic peptide or its derivatives of the present invention have a neurotrophic activity and are useful for the treatment of neuro-degenerative disorders and dementia.

5 Claims, 9 Drawing Sheets

FIG. 1

AMINO ACID SEQUENCE      Ala-Ala-Asp-Ile-Ser-Gln-Trp-Ala-Gly-Pro-Leu

DEDUCED NUCLEOTIDE SEQUENCE 5'-GCA-GCA-GAC-AUA-UCA-CAA-UGG-GCA-GGA-CCA-CUA-3'
```
                              C   C   U   C   C   C       C   C   C   C
                              G   G       U   G               G   G   G   G
                              U   U       U                   U   U   U   U
                                              AGC                         UUA
                                              U                           A
```

PROBE AT THE COMBINATIONS    3'-CTG-TAT-AGT-GTT-ACC-CG-5'

24 DIFFERENT COMBINATIONS         A    G    G    C

A

3'-CTG-TAT-AGC-GTT-ACC-CG-5'

24 DIFFERENT COMBINATIONS         A    G    A    C

A

3'-CTG-TAT-TCG-GTT-ACC-CG-5'

24 DIFFERENT COMBINATIONS         A    G    A    C

A

C-TERMINUS PROBE               3'-TT-ACC-CGT-CCT-GGT-GA-5'

256 DIFFERENT COMBINATIONS        C       G    G    G A

C    C    C

A    A    A

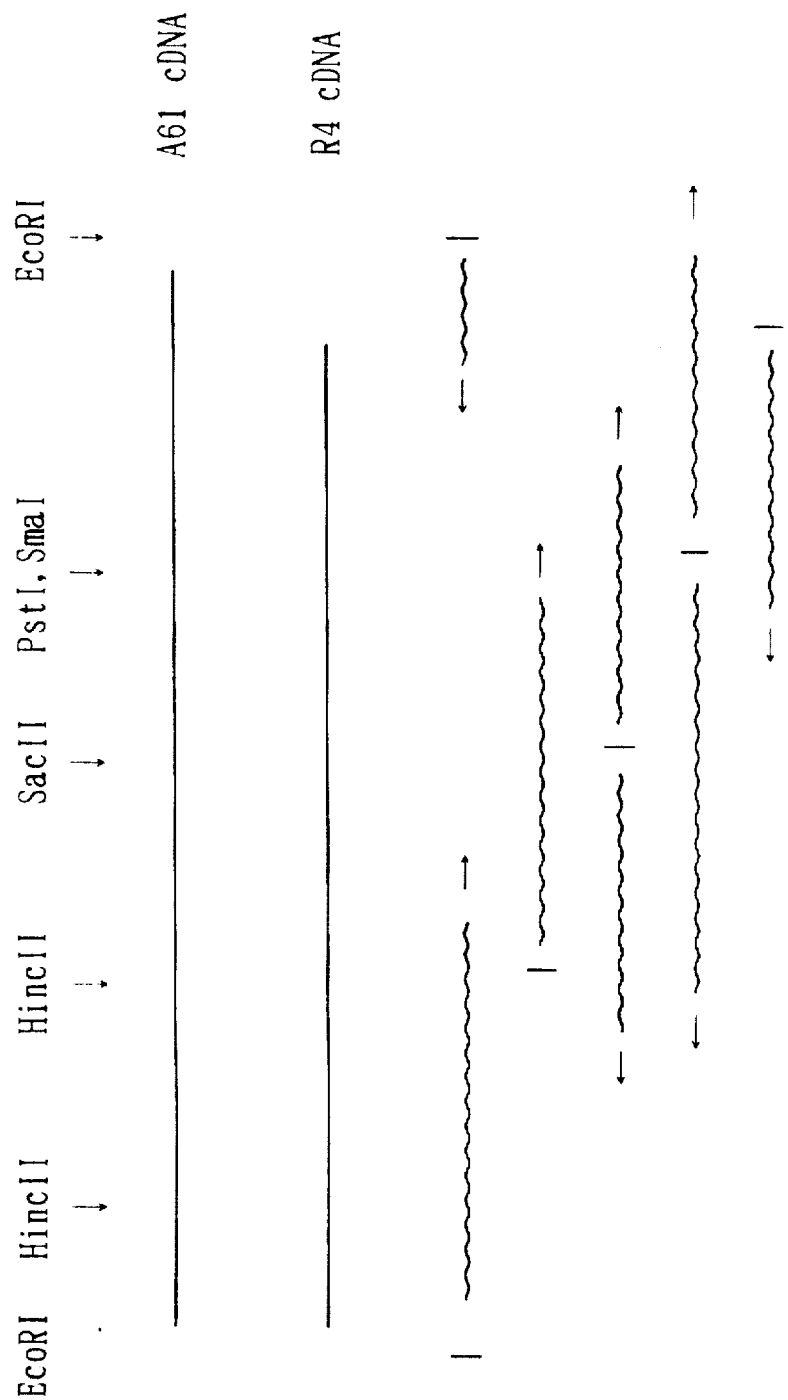

FIG. 3A

```
    Ala Ala Asp Ile Ser Gln Trp Ala Gly Pro Leu Ser Leu Gln Glu
  G GCC GCC GAC ATC AGC CAG TGG GCC GGG CCG CTG TCA CTA CAG GAG

Val Asp Glu Pro Pro Gln His Ala Leu Arg Val Asp Tyr Gly Gly Val
  GTG GAT GAG CCG CCC CAG CAC GCC CTG AGG GTC GAC TAC GGC GGA GTA

Thr Val Asp Glu Leu Gly Lys Val Leu Thr Pro Thr Gln Val Met Asn
  ACG GTG GAC GAG CTG GGC AAA GTG CTG ACG CCC ACC CAG GTC ATG AAT

Arg Pro Ser Ser Ile Ser Trp Asp Gly Leu Asp Pro Gly Lys Leu Tyr
  AGA CCA AGC AGC ATT TCA TGG GAT GGC CTT GAT CCT GGG AAG CTC TAC

Thr Leu Val Leu Thr Asp Pro Asp Ala Pro Ser Arg Lys Asp Pro Lys
  ACC CTG GTC CTC ACA GAC CCC GAT GCT CCC AGC AGG AAG GAC CCC AAA

Phe Arg Glu Trp His His Phe Leu VAL Val Asn Met LyS Gly Asn Asp
  TTC AGG GAG TGG CAC CAC TTC CTG GTG GTC AAC ATG AAG GGC AAC GAC

Ile Ser Ser Gly Thr Val Leu Ser Glu Tyr Val Gly Ser Gly Pro Pro
  ATT AGC AGT GGC ACT GTC CTC TCC GAA TAC GTG GGC TCC GGA CCT CCC

Lys Asp Thr Gly Leu His Arg Tyr Val Trp Leu Val Tyr Glu Gln Glu
  AAA GAC ACA GGT CYG CAC CGC TAC GTC TGG CTG GTG TAT GAG CAG GAG
```

FIG. 3B

Gln Pro Leu Asn Cys Asp Glu Pro Ile Leu Ser Asn Lys Ser Gly Asp
CAG CCT CTG AAC TGT GAC GAG CCC ATC CTC AGC AAC AAG TCT GGA GAC

Asn Arg Gly Lys Phe Lys Val Glu Ser Phe Arg Lys Lys Tyr His Leu
AAC CGC GGC AAG TTC AAG GTG GAG TCC TTC CGC AAG AAG TAC CAC CTG

Gly Ala Pro Cal Ala Gly Thr Cys Phe Gln Ala Glu Trp Asp Asp Ser
GGA GCC CCG GTG GCC GGC ACG TGC TTC CAG GCA GAG TGG GAT GAC TCT

Val Pro Lys Leu His Asp Gln Leu Ala Gly Lys
GTG CCC AAG CTG CAT GAT CAG CTG GCT GGG AAG TAG GGGCGCTGCAGAGCC
CGCAGCCCCGGGGACCCCACAGTACAGTCAAGTCGTATAAAGCATGTCTGTGGGGTGTCCCCC
CACGCCCATCCTTCCTTCCCACCCTCTCATAGGGAGTTCTCAGTTGTGCTAGGTTACAGCTCT
AGGATGTCTTCCACTTTGTCCAGGACCAGGCCCAGTAACATCTTTTGGGGTGGGCTTATCAAT
CCTCCCATCTCGGCTGAGCCCTGACCGCCCAGGTCAGATGGCTGCATAGTTATCAATATTCCT
GGGCTGCTGCTACGCAGTGCTGCTGTGTGGAGGCCAGGCTGTGGAGAGAGACCCTGTTAGCCC
CTTACATCCCAGTGGGATAAGCAAAAGTCACCGGAGTTGCTGGGCGTGTTAAACCTCATCAAA
TACAAATAAAGGGCATTGCATTCAGAAAAAAAAAAAAAAAAAAAAAAAAAAAAAAAAAAAAAA
AAAAAAA

FIG. 4

Ala Ala Asp Ile Ser Gln Trp Ala Gly Pro Leu Ser Leu Gln Glu
Val Asp Glu Pro Pro Gln His Ala Leu Arg Val Asp Tyr Gly Gly
Val Thr Val Asp Glu Leu Gly Lys Val Leu Thr Pro Thr Gln Val
Met Asn Arg Pro Ser Ser Ile Ser Trp Asp Gly Leu Asp Pro Gly
Lys Leu Tyr Thr Leu Val Leu Thr Asp Pro Asp Ala Pro Ser Arg
Lys Asp Pro Lys Phe Arg Glu Trp His His Phe Leu Val Val Asn
Met Lys Gly Asn Asp Ile Ser Ser Gly Thr Val Leu Ser Glu Tyr
Val Gly Ser Gly Pro Pro Lys Asp Thr Gly Leu His Arg Tyr Val
Trp Leu Val Tyr Glu Gln Glu Gln Pro Leu Asn Cys Asp Glu Pro
Ile Leu Ser Asn Lys Ser Gly Asp Asn Arg Gly Lys Phe Lys Val
Glu Ser Phe Arg Lys Lys Tyr His Leu Gly Ala Pro Val Ala Gly
Thr Cys Phe Gln Ala Glu Yrp Asp Asp Ser Val Pro Lys Leu His
Asp Gln Leu Ala Gly Lys

5,759,991

NEUROTROPHIC PEPTIDE DERIVATIVES

CROSS REFERENCE TO RELATED APPLICATION

This is a continuation application of international application No. PCT/JP93/01214 filed on Aug. 27, 1993, which is a continuation-in-part application of patent application Ser. No. 07/873,764 filed on Apr. 27, 1992, now abandoned, and patent application Ser. No. 07/758,043 filed on Sep. 12, 1991, now abandoned, which is a continuation-in-part application of patent application Ser. No. 07/501,217 filed on Mar. 29, 1990, now abandoned.

BACKGROUND OF THE INVENTION

1. Field of the Invention

The present invention relates to polypeptides associated with neurotrophic factor and genes thereof, more particularly, to neurotrophic peptides and derivatives thereof and genes thereof. That is, the present invention relates to neurotrophic peptides (so called neurostimulating peptide) from human origin and derivatives thereof which are useful as drugs, precursor polypeptides from human or rat origin, genes encoding the same, and transformants containing recombinant expression vectors bearing these genes. The invention also relates to compositions for the treatment of neuro-degenerative disorders comprising as effective components these neurotrophic peptides or derivatives thereof.

More specifically, the present invention relates to novel neurotrophic peptides, namely, neurotrophic peptides from human origin having a neurotrophic factor activity corresponding to the neurotrophic peptides from rat hippocampus origin having a neurotrophic factor activity, or neurotrophic peptide derivatives containing a part of the amino acid sequence thereof, or neurotrophic peptide derivatives obtained by modifying the termini of such peptides or derivatives. The present invention also relates to precursor polypeptides containing neurotrophic peptides from rat hippocampus or human origin. The present invention further relates to genes encoding neurotrophic peptides from rat hippocampus or human origin, precursor polypeptides thereof or peptides comprising a part thereof; and bacteria, yeast or mammal cells transformed by recombinant expression vectors having incorporated therein these genes. The invention also relates to compositions for the treatment of neuro-degenerative disorders comprising as effective components the neurotrophic peptides of the present invention or derivatives thereof, precursor polypeptides thereof.

2. Related Art Statement

Various reports have been hitherto made on neurotrophic factors. Among them, hippocampal cholinergic neurotrophic peptide (HCNP) is a neurotrophic peptide composed of 11 amino acid residues which was isolated from hippocampal tissue of neonatal rat by Ojika et al. This peptide enhances production of acetylcholine for rat medial septum nuclei acetylcholinergic neuron (Reference 1). Ojika et al. also discloses HCNP derivatives having a small molecular weight (Reference 2). As proteinaceous factors already isolated and determined for the primary structures, there are nerve growth factor (NGF; Reference 3), brain-derived neurotrophic factor (BDNF; Reference 4) and ciliary neurotrophic factor (CNTF: Reference 5). In recent years, a factor called Neurotrophin-3 (NT-3) showing a high similarity to NGF and BDNF has been cloned (References 6, 7, 8). NGF, BDNF and CNTF are proteinaceous factors having molecular weights of 13,259, 13,511 and 22,660, respectively; cloned NT-3 (NGF-2) is also a protein having the total amino acid number of 119. Therefore, in the case where such factors are used as agents for the treatment of neuro-degenerative disorders, the factors are likely to cause difficult problems about bioavailability, industrial production, etc. In this regard, HCNP obtained from rat is a peptidic factor having 11 amino acid residues and its derivatives have a lower molecular weight as described above. Therefore, these problems are considered to be solved.

However, HCNP obtained in the prior art is a factor from rat brain origin and hence, where HCNP is used for the treatment of neuro-degenerative disorders in higher mammals such as human, it is desired to use the factor derived from the corresponding animal species. It has thus been strongly desired to develop HCNP derived especially from human and its derivatives having a pharmacological activity equivalent to that of HCNP. However, it is the actual situation that any satisfactory compounds have not been obtained yet.

SUMMARY OF THE INVENTION

The present invention solves the foregoing problems in the prior art.

That is, a first object of the present invention is to provide novel neurotrophic peptides (hereinafter sometimes abbreviated as "HCNP") or derivatives thereof which have a neurotrophic activity on acetylcholinergic neurons.

A second object of the present invention is to provide genes encoding the aforesaid neurotrophic peptides.

A third object of the present invention is to provide transformants containing expression vectors bearing the genes described above.

A fourth object of the present invention is to provide novel compositions for the treatment of neuro-degenerative disorders.

In order to solve the foregoing problems, the present inventors performed cloning of the gene encoding precursor protein containing HCNP from rat brain origin for the purpose of determining the amino acid sequence of HCNP derived from human corresponding to the HCNP from rat brain origin.

This is because it is considered to be extremely important to clarify the mechanism of expression of the aforesaid precursor protein containing HCNP and processing of the thus produced protein and also from these aspects, cloning of the gene encoding the precursor protein was required.

More specifically, survey on the gene encoding the precursor protein was performed from cDNA library prepared using mRNA prepared from rat hippocampal tissue, using polyclonal antibody to rat HCNP composed of the 11 amino acids described above.

As the result, the precursor gene containing rat HCNP have been successfully isolated from the total genes which are acting on cells in the hippocampal tissue of neonatal rat. The present invention has thus come to be attained.

Furthermore, the gene encoding human precursor polypeptide has also been successfully isolated from the gene encoding rat precursor polypeptide. In addition, a neurotrophic factor activity was noted in human peptide composed of 11 amino acids corresponding to rat neurotrophic peptide. The present invention has thus been accomplished.

That is, the present invention is directed to:

(1) a gene encoding a neurotrophic peptide represented by SEQ ID NO: 2;

(2) a gene encoding a neurotrophic peptide represented by SEQ ID NO: 17;

3

(3) a gene encoding a polypeptide represented by SEQ ID NO: 4;

(4) a gene encoding a polypeptide represented by SEQ ID NO: 15;

(5) a neurotrophic peptide having an amino acid sequence represented by SEQ ID NO: 17 or neurotrophic peptide derivatives having a neurotrophic activity comprising a part of the amino acid sequence which part has at least said -Lys-Trp- sequence;

(6) neurotrophic peptide derivatives having a neurotrophic activity which have been modified at the N terminus and/or C terminus of the neurotrophic peptide or neurotrophic peptide derivatives recited in (5);

(7) a precursor polypeptide represented by SEQ ID NO: 4;

(8) a precursor polypeptide represented by SEQ ID NO: 15;

(9) bacteria, yeast or mammal cell transformed by a recombinant expression vector bearing said gene; and,

(10) a composition comprising as an effective ingredient the aforesaid neurotrophic peptide or neurotrophic peptide derivatives.

BRIEF DESCRIPTION OF THE DRAWINGS

FIG. 1. SEQ ID NOS: 1 and 2, shows a sequence of oligonucleotide probe used for screening of clone.

Among nucleotide sequences deduced from the amino acid sequence of neurotrophic peptide derived from rat hippocampus, the probe region used is illustrated.

1) Probes of 72 different kinds present at the center of the nucleotide sequence were synthesized. In this case, 3 kinds of the probe group composed of 17 nucleotides in 24 different combinations illustratively shown as the probes at the center were synthesized and the equimolar number was mixed to form the probe.

2) The probe at the C terminus is a probe mixture of 16 nucleotides in 256 different combinations.

FIG. 2 shows restriction enzyme map of the neurotropic peptide precursor gene from rat hippocampus origin and strategy for determining nucleotide sequence.

In the figure, digestion pattern of the precursor gene clone (A6lcDNA) with restriction enzymes is shown. In A6lcDNA (fragment of about 1 Kb with Eco RI), cleavage sites with Hinc II, Sac II, Pst I and Sma I are present. Using these cleavage sites, the cone was subjected to subcloning and the nucleotide sequence in the zone shown by wavy lines was determined. Bold line in A6cDNA shows open reading frame found as the result of determining the nucleotide sequence.

FIGS. 3A and 3B, SEQ ID NO: 3, shows the entire nucleotide sequence of clone A6lcDNA containing the neurotrophic peptide precursor gene from rat hippocampus origin.

The amino acid sequence deduced from the nucleotide sequence is also shown. From the N terminals of the open reading frame, sequence of 11 amino acids having a neurotrophic factor activity was present. The number of amino acids constructing the open reading frame was 186. In the figure, the under line indicates poly(A) addition signal. ATG sequence which is a translation initiation codon is not included in the open reading frame.

FIG. 4, SEQ ID NO: 4, shows amino acid sequence deduced from the nucleotide sequence shown in FIGS. 3A and 3B. The translation initiation codon is not included in this amino acid sequence.

4

Figure 5:
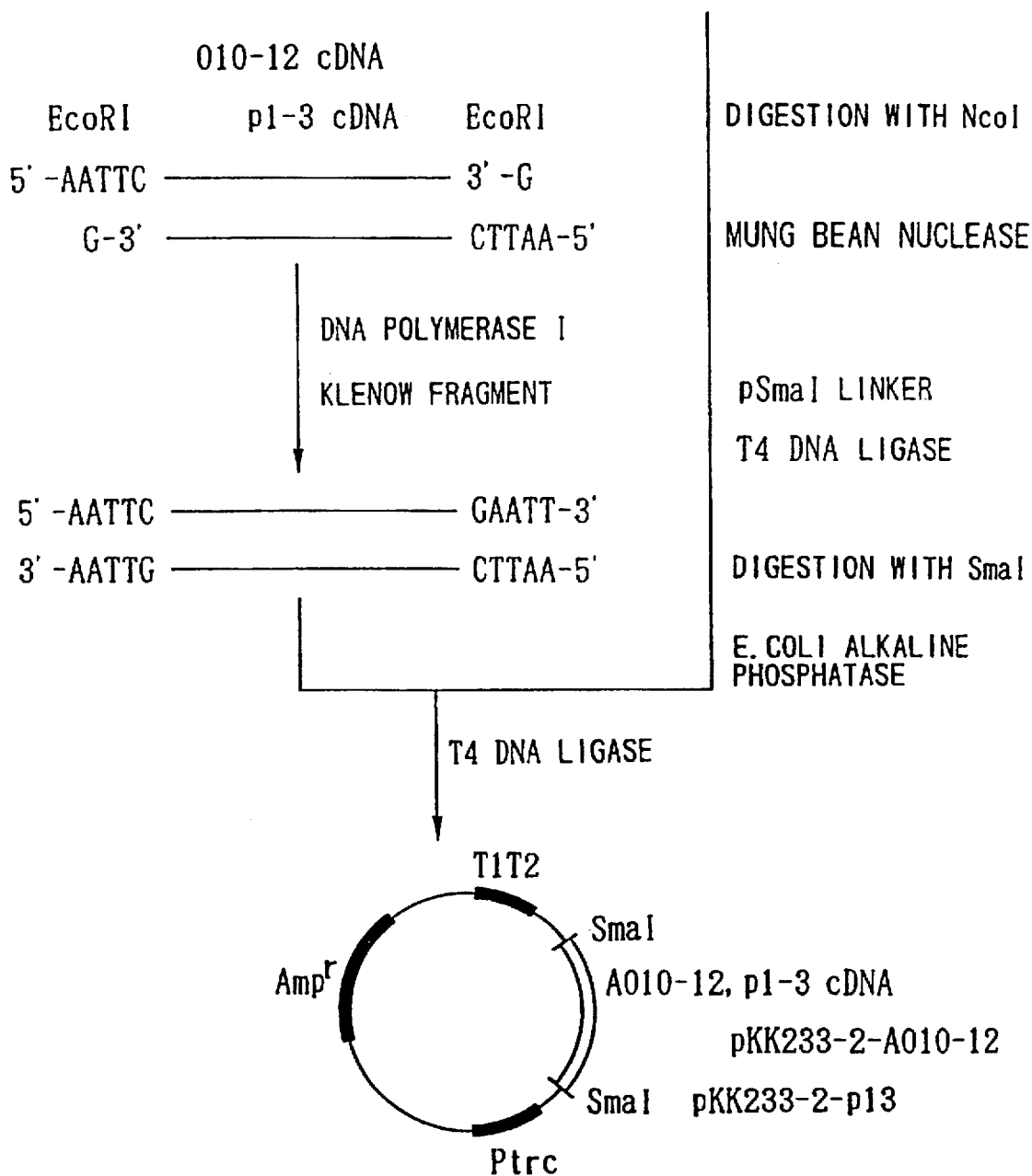

FIG. 5 shows the steps of inserting the neurotrophic peptide precursor gene derived from rat and human into *E. coli* expression vector pKK233-2 derivative.

The Eco RI termini of the neurotrophic peptide precursor gene (AO10-12cDNA) of rat hippocampus origin were rendered smooth with DNA polymerase I (Klenow fragment) to transduce into *E. coli* expression vector pKK233-2. *E. coli* expression vector pKK233-2 was rendered smooth by digesting the same with Nco I and then treating with Mung bean nuclease, thereby to insert Sma I linker. The so constructed vector was digested with Sma I and then treated with phosphatase to transduce the precursor gene described above. The cloned recombinant vectors were named pKK233-2-AO10-12 and pKK233-2-p13.

Figure 6:
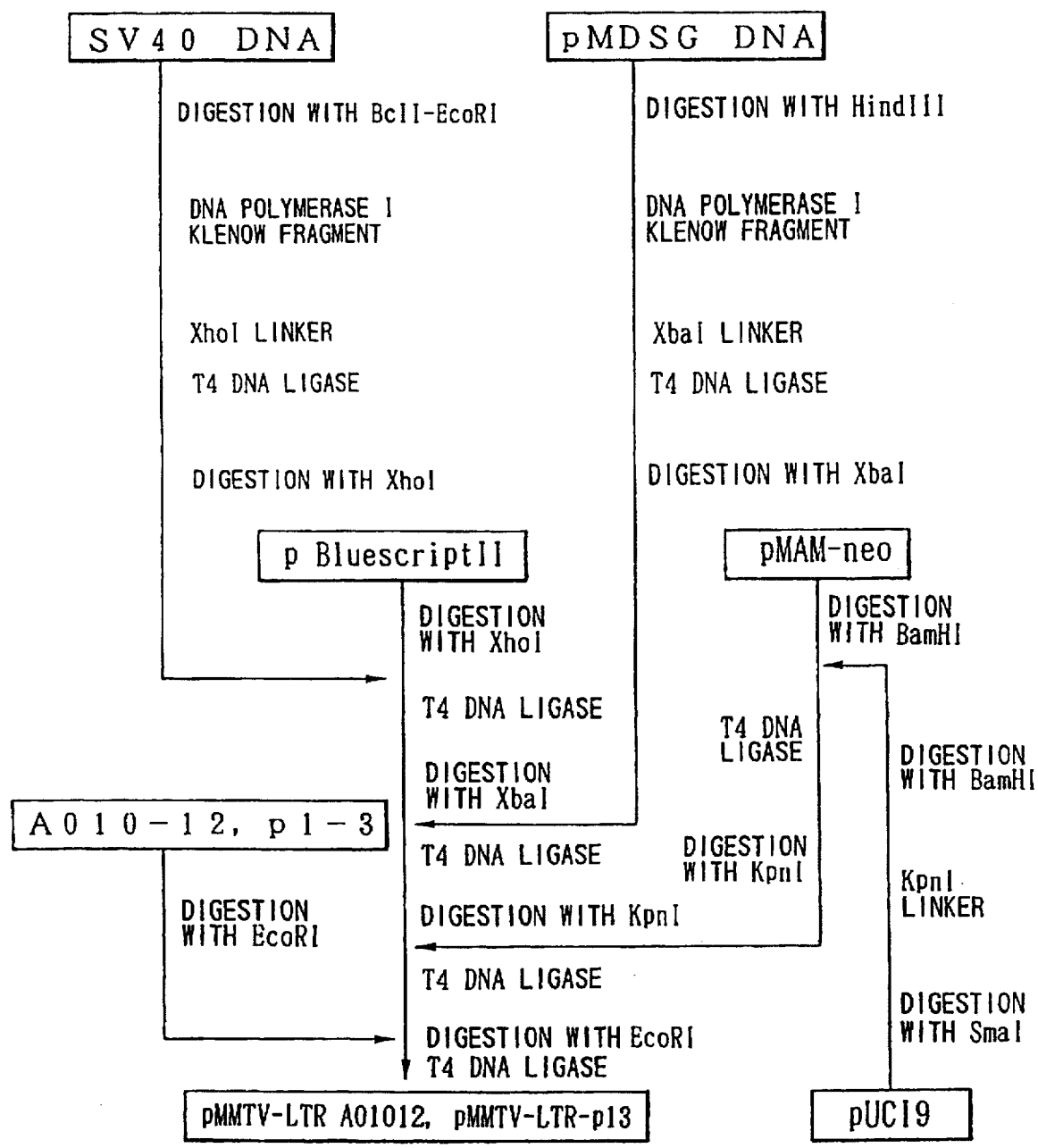

FIG. 6 shows steps of transducing the neurotrophic peptide precursor genes derived from rat and human hippocampus into eukaryote expression vector.

The expression vector transduced was constructed by the following procedures. After pMDSG DNA bearing MMTV-LTR was digested with Hind III, 1.4 Kb of DNA fragment bearing MMTV-LTR was treated with DNA polymerase I (Klenow fragment) to render smooth. Xba I linker was added and inserted into Xba I site of pBluescript II. Furthermore after SV40DNA was digested with Bcl I-Eco RI, 1 Kb DNA fragment having poly(A) additional signal was rendered smooth likewise. Xho I linker was added followed by inserting pBluescript II into Xho I site. Then 2.6 Kb of Bam HI fragment of pMAM-neo containing neomycin resistant gene was inserted into Bam HI site of pUC19, previously integrated Kpn I linker into Sma I site. 2.6 Kb of Kpn I digests were inserted into Kpn I site of constructed expression vector. AO10-12 and p1-3 genes were inserted into the Eco RI site of the thus constructed expression vector and the cloned recombinant vectors were named pMMTV-LTR-AO10-12 and pMMTV-LTR-p13.

Figure 7:
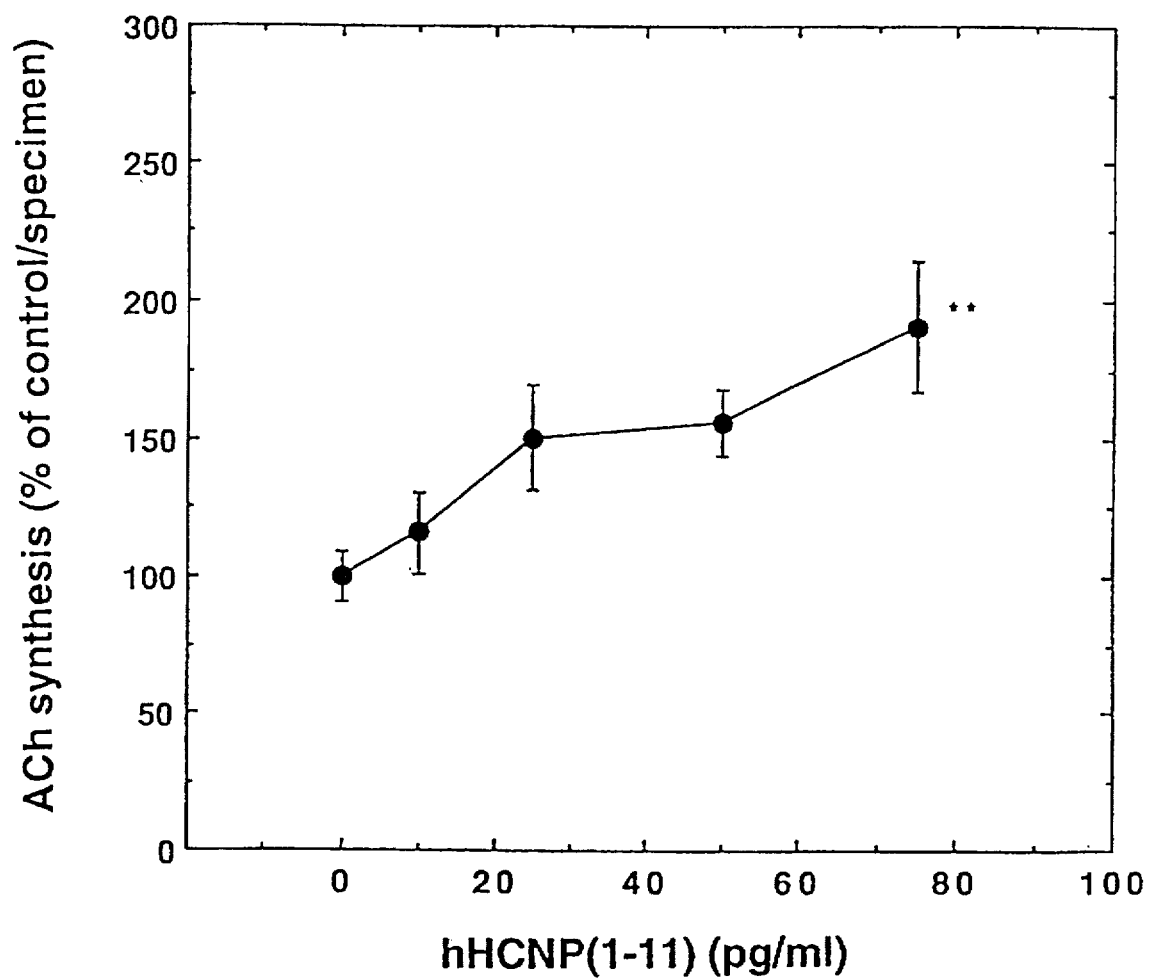

FIG. 7 shows effect of hHCNP(1-11) obtained in Example 12 on ACh (acetylcholine) synthesis Mean±S.E. **P<0.01).

Figure 8:
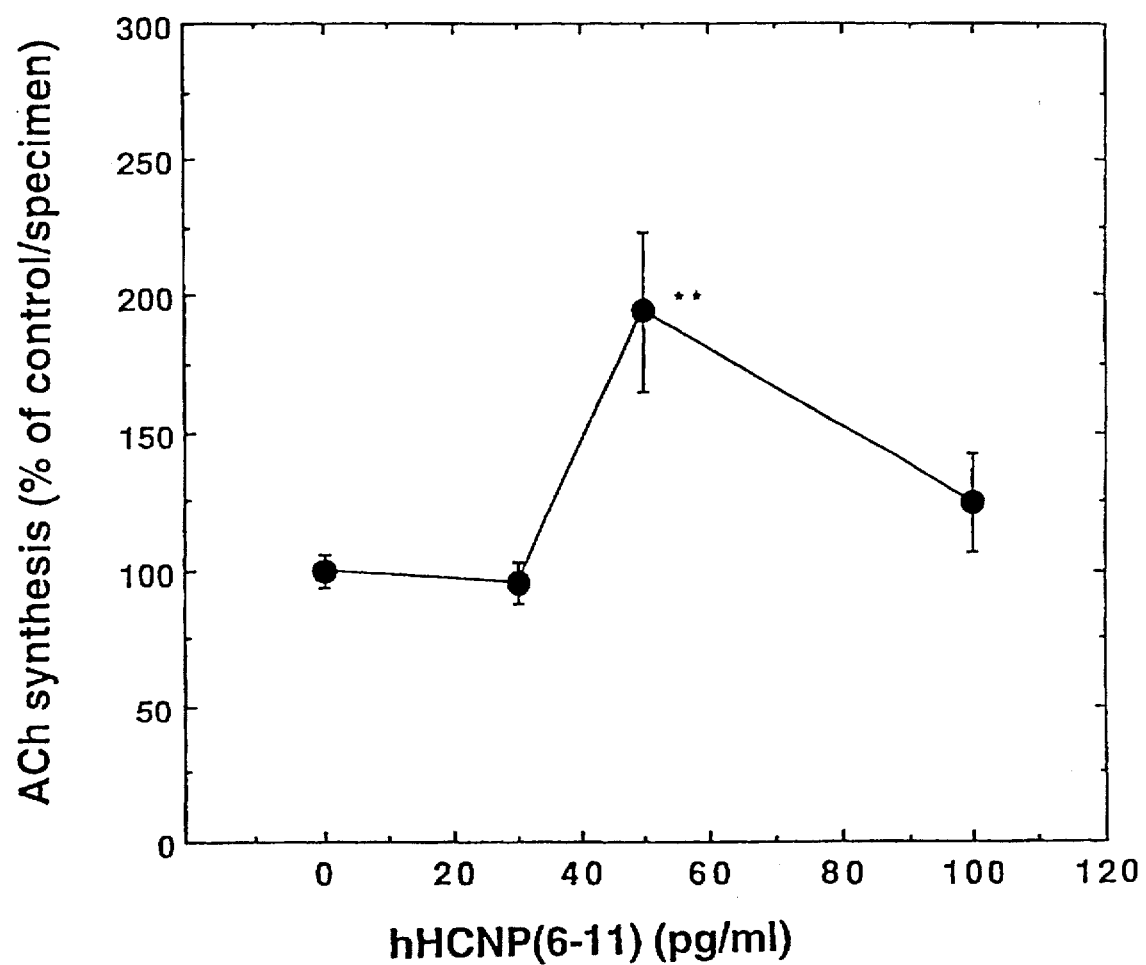

FIG. 8 shows effect of hHCNP (6-11) obtained in Example 14 on ACh synthesis (Mean±S.E. **P<0.01).

DETAILED DESCRIPTION OF THE INVENTION

The gene encoding the rat precursor polypeptide of the present invention is obtained by preparing mRNA from the hippocampal tissue of neonatal rat aging 12 days after birth in which the presence of neurotrophic peptide derived from rat hippocampus was noted, converting into double stranded cDNA in a conventional manner, synthesizing a protein encoded to cDNA in *E. coli*, and isolating the clones showing reactivity with an antibody to the neurotrophic peptide from rat hippocampus origin.

The total RNA from the hippocampal tissue of neonatal rat described above may be prepared in a conventional manner already used for cloning of several physiologically active proteins. For example, there is a method which extracts the total RNA from the cells in the presence of surfactants such as SDS, NP-40, Triton-X100, etc. or in the presence of phenol (References 10, 11). In this case, it is desired to add RNase inhibitors such as vanadium complexes, heparin, bentonite, diethyl pyrocarbonate, etc. for the purpose of decomposition of RNA by RNase. The total RNA may also be obtained by homogenizing cells by physical means using a homogenizer, etc., treating the cells with guanidine thiocyanate and then precipitating the total RNA by cesium chloride density gradient centrifugation (Reference 10, 12, 13). Next, polyadenylated mRNA is purified from the total RNA obtained by any one of the methods described above. For the purification, an affinity column packed with oligo (dT)-cellulose, poly U-Sepharose obtained by binding poly U thereto, etc. may be used (References 14, 15). Alternatively, where the size of mRNA is already revealed or fractionation is desired based on the size of mRNA, it is possible to use sucrose density gradient centrifugation (Reference 16), agarose gel electrophoresis, gel filtration using a column, etc. The thus obtained poly (A) mRNA is confirmed if it encodes the desired protein. For the confirmation, some of the following methods are applied.

1) The prepared mRNA is translated directly into a protein and physiological property of the thus produced protein is examined. In this case, it is conventional to either introduce mRNA into oocyte of *Xenopus laevis* (References 17, 18) or synthesize a protein in vitro using rabbit reticulocyte or wheat germ extract (Reference 16).

2) Single stranded cDNA is synthesized using mRNA as a template and then double stranded cDNA is synthesized. The double stranded cDNA is incorporated into an appropriate vector which is recombined with a host such as *E. coli* or eukaryote, etc. to introduce expression vector. Where an expression vector is used as the vector, expression is effected in the host in which the protein encoded by cDNA is transduced and the desired clone can be selected using an antibody to the desired protein. In addition, a partial amino acid sequence of the protein previously prepared may be determined, oligonucleotide is synthesized and the desired clone may be selected using the oligonucleotide as a probe.

Firstly, using mRNA as a template, single stranded cDNA complementary to mRNA is synthesized by reverse transcriptase (derived from avian myeloblastosis virus (AMV) or derived from murine leukemia virus (Mo-MLV)) in the presence of dATP, dGTP, dCTP and dTTP using oligo (dT) primer (References 19, 20) or a random primer composed of 6 bases (References 21, 22). Then, after mRNA is digested by an alkali treatment, double stranded cDNA is synthesized by reverse transcriptase or DNA polymerase using single stranded cDNA as a template. The double stranded cDNA may also be synthesized by directly acting RNaseH and *E. coli* DNA polymerase I (Reference 19). Then, the both ends of the synthesized double stranded cDNA is rendered smooth in any case, using any enzyme of S1 nuclease, T4 DNA polymerase and *E. coli* DNA polymerase I (Klenow fragment), etc. In order to insert into an appropriate vector, the thus synthesized double stranded cDNA with blunt ends is modified at the ends thereof by adding chemically synthesized DNA such as a linker or adaptor (References 22, 23, 24, 25, 26, 27, 28, 29) or adding dG or dC chain by terminal deoxynucleotidyl transferase (References 30, 31).

The thus obtained double stranded cDNA is incorporated into a vector and EK1 type plasmid vectors such as pBR322, pUC19, pSC101, ColE1, Honjo vector, etc., or lambda phage vectors such as λgt10, λgt11, λgtWES, λzap, etc. are often used as such a vector. Where the double stranded cDNA is incorporated into these vectors, the double stranded cDNA can be ligated with the vectors by acting T4 DNA ligase in the presence of ATP.

After the double stranded cDNA is incorporated into the appropriate vector described above, *E. coli* (AG-1, HB101, JM109, DH5, C600, Y1090, LE392 strains; etc.) is transformed to obtain DNA group of transformants (hereafter referred to as cDNA library).

Where the double stranded cDNA is incorporated into a plasmid vector to transform *E. coli*, competent cells which can incorporate this DNA therein are collected at the exponential growth phase and transformed by the method reported by Hanahan in detail, namely, in the presence of $CaCl_2$, $MgCl_2$ or RbCl (References 32, 33). Further where the double stranded cDNA is incorporated into a phage vector to transform *E. coli*, DNA ligated by T4 DNA ligase is introduced into phage particles by in vitro packaging and infected to *E. coli* thereby to effect transformation (Reference 10).

*E. coli* bearing the precursor gene encoding the neurotrophic peptide of rat hippocampus origin can be transformed and selected using any one of the following two methods.

1) A nucleotide sequence is deduced from the amino acid sequence of SEQ ID NO: 2 and chemically synthesized. The nucleotide sequence is used as a probe. In this case, however, one codon does not always correspond to one amino acid (wobbling) and therefore, it is desired to use a region having the smallest number of combinations in nucleotide sequence as an oligonucleotide probe. It is also desired that a plurality of regions be used as the oligonucleotide probe. Transformants may be selected by colony or plaque hybridization, etc. (References 10, 23, 24).

2) Based on the amino acid sequence of SEQ ID NO: 2, an oligopeptide is chemically synthesized; the synthesized oligopeptide is bound to a protein such as bovine serum albumin, etc. An antibody to the thus obtained protein complex is prepared from rabbit.

Where the double stranded cDNA is inserted into a gene encoding a protein such as β-galactosidase, etc. upon incorporation of the double stranded cDNA into a vector, the protein encoded by cDNA is expressed in such a form that the protein is fused to the protein such as β-galactosidase, etc. Therefore, the cDNA-incorporated recombinant expression vector is transfected to host *E. coli* to obtain transformants and a protein produced in the transformants is fixed on a membrane filter, etc. by Western blotting, whereby a transformant bearing the desired gene can be isolated (References 23, 25, 26, 27, 28, 29). The desired transformant can be detected in a simple manner by detecting the rabbit antibody bound to the protein fixed on a membrane filter. For detecting the rabbit antibody, some methods described below may be used.

1) Biotinized anti-rabbit Ig antibody is reacted with rabbit antibody bound to the protein. Next, avidin or streptoavidin having a high binding affinity with biotin is bound to the reaction product. By previously binding an enzyme such as peroxidase, etc. to avidin and streptoavidin, the desired transformant can be obtained by the enzyme reaction (References 34, 35).

2) Protein A molecule having a high binding affinity to Ig antibody is reacted with rabbit antibody bound to the desired protein. In this case, by previously labeling protein A with an isotope, the desired transformant can be detected by autoradiogram (Reference 23).

3) By reacting anti-rabbit Ig antibody bound to an enzyme such as peroxidase, etc. with rabbit antibody bound to the protein, the desired transformant can be obtained by the enzyme reaction (References 36, 37, 38).

It is possible to detect the desired transformant by any of the methods but Method 1) is particularly preferable because of the lowest background and the highest sensitivity.

The rat precursor gene containing the rat hippocampal neurotrophic peptide of the present invention can be cloned as described above to give a gene encoding the amino acid sequence represented by SEQ ID NO: 4. In the amino acid sequence represented by SEQ ID NO: 4, 134 position at amino acid is Glu but this position may be Lys. Such a gene is exemplified by nucleotide sequence shown by SEQ ID NO: 3. The protein corresponding to the thus obtained precursor gene showed extremely high homology (84.4%) to bovine phosphatidylethanolamine binding protein (Reference 9). The rat hippocampal neurotrophic peptide was present at the N terminal of the precursor protein.

With respect to rat hippocampal neurotrophic peptide and its derivatives having a lower molecular weight, their structures have already revealed by References 1 and 2 as described above but nothing has been reported on genes thereof. The present inventors have found the nucleotide sequence shown by SEQ ID NO: 1 as a gene encoding the amino acid sequence (SEQ ID NO: 2) of rat hippocampal neurotrophic peptide by clarifying the precursor gene as described above.

Using as a probe the thus obtained rat precursor gene cDNA containing the rat hippocampal neurotrophic peptide, it is possible to perform cloning of human cDNA gene corresponding to the rat gene.

In order to survey human cDNA gene, it is necessary to prepare any of cDNA libraries derived from various organs such as human embryonal brain, adult brain, placenta and the like. It is difficult to acquire these human tissues but now cDNA libraries can be purchased.

In most cases, these cDNA libraries are purchased as phage particles where cDNA has been incorporated into a λ phage vector such as λgt10, λgt11, λzap, etc. These phage libraries may be infected with appropriate E. coli (C600, Y1088, Y1090, XL1-Blue, etc.) to transform E. coli. E. coli bearing human cDNA gene corresponding to the precursor gene containing the gene encoding rat hippocampal neurotrophic peptide may be selected in a simple manner by plaque hybridization, using as a probe isotope-labeled rat precursor gene cDNA fragment. The probe is prepared by purifying cDNA fragment containing the rat precursor gene and labeling with $^{32}P$ by nick translation or random prime labeling.

By comparing the sequence of human cDNA gene thus obtained with homology to rat precursor cDNA gene, the sequence of human neurotrophic peptide corresponding to the region where the sequence of rat neurotrophic peptide is present can be determined.

The present inventors have succeeded in isolating human precursor gene from the rat precursor gene and determining its structure. The human precursor gene of the present invention encodes the amino acid sequence shown by SEQ ID NO: 15 and an example of such gene includes the gene shown by SEQ ID NO: 14. By comparing the rat precursor gene with human precursor gene in homology, it was presumed that human HCNP would take the following amino acid sequence structure (SEQ ID NO: 17) and would be a peptide quite dissimilar to rat HCNP. An example of the gene encoding such human HCNP includes the gene shown by SEQ ID NO: 16.

H-Pro-Val-Asp-Leu-Ser-Lys-Trp-Ser-Gly-Pro-Leu-OH

[hereinafter this human-derived HCNP peptide is sometimes referred to as hHCNP (human derived hippocampal cholinergic neurotrophic peptide)].

In fact, a neurotrophic activity similar to rat-derived HCNP was noted in this peptide and the present invention has thus been accomplished.

The neurotrophic activity (also called neurotrophic factor activity) refers to, for example, an action of regulating differentiation and maturation of neuronal cells, namely, an action of accelerating the acetylcholine synthesis in the tissue of medial septum nuclei which is rich in cholinergic neurons.

The DNA fragments bearing the genes encoding the thus cloned precursor polypeptide containing neurotrophic peptide from rat hippocampus or human origin are incorporated into appropriate vectors, respectively to transform prokaryote such as E. coli or B. subtilis, etc. As the vector in which the desired gene is incorporated, it is generally preferred to use a plasmid vector having replicon and regulation sequence which is obtained from a species compatible with a host cell. The plasmid vector generally carries a replication origin (Ori) and a marker gene, for example, chemical-resistant gene, which enables to phenotype selectivity of a transformant.

For example, strains such as HB101, JM109, etc. derived from E. coli K 12 strain can be transformed by pBR322 constructed from R factor obtained from E. coli or derivatives thereof. pBR322 bears a gene resistant to ampicillin and tetracycline and can thus easily detect a transformant which has acquired chemical resistance (Reference 39).

Further by incorporating into these recombinant vectors an appropriate promoter and a sequence participating in expression of a gene, the precursor polypeptide encoded by the recombinant DNA fragment can be expressed in host cells such as bacteria, yeast, mammal cells, etc.

As the promoter used for expression of a gene in host cells of bacteria, there are promoters for β-lactamase, lactose gene, tryptophane gene of E. coli, etc. (References 27, 40, 41, 42, 43). Any of the promoters for these genes can be used for expression of the precursor protein of the present invention containing the neurotrophic peptide of rat hippocampus and human origin.

In addition to prokaryotes, eucaryotic microorganisms such as yeast may also be used as host cells. Saccharomyces cerevisiae is an eucaryotic microorganisms which is used most advantageously. Other are also usable as host cells.

Plasmid YRp7 is most conveniently used for gene expression in yeast (References 44, 47). This plasmid contains trp1 gene which enables to phenotype selectivity and make it possible to identify a transformant, in the case of using yeast mutant, PEP4-1, etc. which has lost proliferation ability in the presence of tryptophane.

As a promoter compatible with yeast which is required for gene expression in yeast, there are 3-phosphoglycerate kinase (Reference 46) and many other gene promoters such as genes for glycolytic pathway enzyme (References 47, 48). Also in eukaryote, poly(A) sequence is added at the 3' end of mRNA transcribed from a gene, with a few exceptions. Transcription is terminated by inserting the DNA fragment having a signal for adding this poly(A) sequence (Reference 49) into the 3' end of the gene expressed.

Where a gene is expressed in cells derived from eukaryotic organisms, it is also possible to use cells derived from vertebrates such as mammals, invertebrates such as insects or derived from plants, as host cells. For the purpose of gene expression expressed in mammals as in the present invention, however, it is more advantageous to use cells of vertebrate origin as host cells. The cells of vertebrate origin used for gene expression may be either primary culture cells obtained from animal tissues or established cultured cells but, the latter cells are considered to be more preferable expression system because of easy handling.

As examples of host cell lines frequently used presently for a variety of experiments for expression of genes, there are Namalwa cells derived from human Burkitt's lymphoma, Vero cells and CV-1 cells which are kidney cells derived from African green monkey, COS-1 and COS-7 cells of SV40 transformants which are kidney cells derived from African green monkey, CHO cells derived from Chinese hamster ovary cells, BHK cells of neonatal syrian hamster kidney cells, MDCK (NBL-2) cells derived from dog kidney cells, NIH/3T3 and Balb/3T3 cells derived from mouse fetal fibroblast, 3Y1 cells derived from rat fetal fibroblast, etc. As a principle, any cell line is usable so long as the promoter for expressing a gene is compatible with the host cell.

As described above, the vector for expressing a gene in a variety of cultured cell lines contains a promoter for transcription in the 5' upstream region of a gene expressed and poly(A) additional signal sequence. If necessary and desired, the vector contains a replication origin capable of autonomic proliferation in eukaryote and the enhancer region which is a trans-activation factor binding site of transcription.

Where a gene is expressed in a mammalian cell, promoter of virus origin and a promoter derived from a certain chromosomal gene compatible with the cell in which the gene is transduced are used as a promoter for the expression vector. Examples of the promoter of virus include SV 40 from monkey, herpes simple virus, polyoma virus and adenovirus. In addition, long terminal repeat (LTR) which is a promoter derived from retrovirus (Rous sarcoma virus RSV, murine leukemia virus MLV, murine mammary tumor virus MMTV, etc.) may also be used widely.

In recent years, a method is described which virus particles transduced the desired gene into a retrovirus derivative vector are produced in the presence of retrovirus acting as a helper. The transduced virus is infected to the host cells with virus thereby to incorporate the gene into the host chromosome and express the desired gene (Reference 50).

As the origin of replication, there are used exogenous origins derived from viruses such as SV40, polyoma, adeno, bovine papiloma, etc. and they are used transient expression of the gene in such a state that the gene is not incorporated into the chromosome of the host cell. In general, where a recombinat DNA without an exogenous origin is transduced into an eukaryote, recombinant DNA fails to perform autonomous replication but is incorporated into the host chromosome. The replication mechanism of the recombinant DNA is governed by that of the host chromosome.

The cell transformed by the desired gene may be identified using as an index, by having acquired phenotype selectivity of transformants such as chemical resistance and viability in selective medium. The gene which can be a marker thereof is either contained the expression vector in which the desired gene has been transduced or contained in another vector containing the marker gene alone. In the latter case, the marker gene is co-transfected into a host cell with the expression vector bearing the desired gene.

As a resistant gene which can be a marker for phenotypic selectivity, a neomycin-resistant gene is frequently used and a cell showing resistance to neomycin (Geneticin: G418) is identified as a transformant (Reference 51). Selectivity of phenotype in selective medium is effected by introduction of HPRT (References 52, 53) or TK gene (References 54, 55) as a marker for hypoxanthine/guanine phosphoribosyl transferase (HPRT)-deficient or thymidine kinase (TK)-deficient mutant culture cell line. As selective medium, HAT medium (containing hypoxanthine, aminopterin or amethopterin (also called methotrexate) and thymidine) is used. Since aminopterin inhibits biosynthesis of purine or pyrimidine, deficient mutant cell cannot proliferate in HAT medium but when chromosome carrying HPRT or TK is retained, the strains can proliferate in HAT medium. In addition, xanthine-guanine phosphoribosyl transferase (Eco gpt) may also be used as a marker gene (Reference 53). Micophenolic acid inhibits synthesis of GMP in animal cells to kill the cells. Eco gpt synthesizes GMP from xanthine in a medium but animal cells cannot utilize the xanthine. Therefore, only a transformant having introduced therein Eco gpt gene can selectively proliferate even after treatment with micophenolic acid.

For transfection of a gene to mammal cells, there may be generally used a method for DNA-calcium phosphate coprecipitation (References 54, 56), a method for protoplast fusion using polyethylene glycol (Reference 57) and the like. Furthermore, a method for electrically transfecting a gene to a host cell using electric pulse (References 58, 59) or a method for physically transfecting a gene directly to a cell using a micromanipulator (Reference 60) may also be used.

The human-derived neurotrophic peptide of the present invention has an amino acid sequence (SEQ ID NO: 17) represented by formula I described hereinafter and as the derivatives thereof, there are neurotrophic peptide derivatives comprising a part of the amino acid sequence which part has at least the -Lys-Trp- sequence and having a neurotrophic activity, and human-derived neurotrophic peptide derivatives obtained by modifying the N-terminal and/ or C terminal thereof.

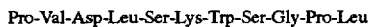

Pro-Val-Asp-Leu-Ser-Lys-Trp-Ser-Gly-Pro-Leu  (I)

Hereinafter the human-derived neurotrophic peptide derivatives of the present invention are described in more detail. The human-derived neurotrophic peptide derivatives of the present invention refer to peptidic derivatives in which the structure of the human neurotrophic peptide represented by formula (I) is modified or converted by means of derivation such as fragmentation and N-terminal modification and/or C-terminal modification, singly or in combination.

In more detail, the human-derived neurotrophic peptide derivatives of the present invention refer to straight-chain peptidic derivatives represented by general formula (II) described below.

X-Z-Y  (II)

In the formula, X represents H, various acyl groups, various sulfonyl groups, or various residues for completing a urea skeleton or urethane skeleton together with the amino group in the amino acid residues to which X is bound.

Specific examples of X are H, or a group represented by chemical formula 1:

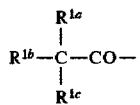

[wherein $R^{1a}$ is H, an unsubstituted or substituted alkyl, hydroxy, —COOH, an aryl, a $C_1$–$C_4$ alkoxy, a halogen atom, —CONR$^2$R$^3$ wherein each of $R^2$ and $R^3$ independently represents H or a $C_1$–$C_4$ alkyl, or a heterocyclic group; $R^{1b}$ represents H, an unsubstituted or substituted alkyl or a halogen atom; and $R^{1c}$ is H, a $C_1$–$C_4$ alkyl or a halogen atom]; a group represented by chemical formula 2:

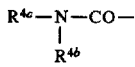

[wherein $R^{4a}$ is H, a $C_1$–$C_4$ alkyl or an aryl; and $R^{4b}$ represents H or a $C_1$–$C_4$ alkyl]; a group shown by:

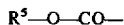

[wherein $R^5$ is an unsubstituted or substituted alkyl or an aryl]; a group shown by:

[wherein $R^6$ is H, an aryl or a heterocyclic group]; a group shown by:

[wherein $R^7$ is an unsubstituted or substituted alkyl or an aryl]; etc.

Y represents OH or a variety of residues for forming an amido or ester group together with the carbonyl group in the amino acid residues to which Y is bound.

Specific and representative examples of Y include a group represented by chemical formula 3:

[wherein $R^{8a}$ is H, an unsubstituted or substituted alkyl, hydroxy, an aryl or a heterocyclic group; and $R^{8b}$ represents H or an unsubstituted or substituted alkyl]; or a group represented by formula:

[wherein $R^9$ is H, an unsubstituted or substituted alkyl, an aryl or a heterocyclic group]; or a group represented by chemical formula 4:

[wherein $R^{10a}$ and $R^{10b}$ form a nitrogen-containing saturated heterocyclic ring together with N]; etc.

Z represents a partial amino acid sequence of hHCNP comprising at least the -Lys-Trp- sequence obtained by any one of fragmentation for reducing amino acid residues from the N-terminus of the amino acid sequence of hHCNP, fragmentation for reducing amino acid residues from the C-terminus and fragmentation for reducing amino acid residues from both N-terminus and C-terminus, or the total amino acid sequence of hHCNP. In more detail, Z represents an amino acid sequence represented by general formula:

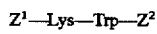

[wherein $Z^1$ represents Pro-Val-Asp-leu-Ser, Val-Asp-Leu-Ser, Asp-Leu-Ser, Leu-Ser, Ser or a single bond and $Z^2$ represents Ser-Gly-Pro-Leu, Ser-Gly-Pro, Ser-Gly, Ser or a single bond]. Most preferred examples of Z include the following:

| | |
|---|---|
| Pro-Val-Asp-Leu-Ser-Lys-Trp-Ser-Gly-Pro-Leu, | SEQ ID NO:17; |
| Val-Asp-Leu-Ser-Lys-Trp, | SEQ ID NO: 18; |
| Leu-Ser-Lys-Trp-Ser, | SEQ ID NO: 19; |
| Lys-Trp-Ser-Gly-Pro-Leu, | SEQ ID NO: 20; |
| Lys-Trp | |

The term "alkyl" used in the present invention means a branched and straight saturated aliphatic hydrocarbon group having a specific number of carbon atoms. For example, $C_1$–$C_4$ alkyl means methyl, ethyl, propyl, butyl, isopropyl, isobutyl, t-butyl, etc.

The term "alkoxy" means an alkyl group having a specific number of carbon atoms which is bound via an oxygen atom. For example, $C_1$–$C_4$ alkoxy means methoxy, ethoxy, propoxy, butoxy, etc.

The term "halogen atom" means fluoro, chloro, bromo and iodo.

The term "aryl" is used to mean phenyl, naphthyl or anthryl, etc. which may optionally be substituted with 1 to 3 groups independently selected from the group consisting of: $C_1$–$C_8$ alkyl, amino, mono- or di-$C_1$–$C_4$ alkylamino, amino-$C_1$–$C_8$ alkyl, mono- or di-$C_1$–$C_4$ alkylamino-$C_1$–$C_8$ alkyl, guanidino, $C_1$–$C_4$ alkylguanidino, guanidino-$C_1$–$C_8$ alkyl, $C_1$–$C_4$ alkylguanidino-$C_1$–$C_8$ alkyl, hydroxyl, hydroxy-$C_1$–$C_8$ alkyl, $C_1$–$C_4$ alkoxy, —$CO_2H$, carboxy-$C_1$–$C_8$ alkyl, halogen atom, $NO_2$, $CF_3$ and —$CONR^2R^3$ [$R^2$ and $R^3$ have the same significances as described above] and the like. The term "$C_1$–$C_4$ alkylguanidino" means a guanidino group in which the guanidino nitrogen atom is alkylated by one or two $C_1$–$C_4$ alkyl groups.

The term "heterocyclic group" is used to mean a saturated or unsaturated 3- to 8-membered monocyclic or 9- to 10-membered fused heterocyclic group. The heterocyclic group is composed of carbon atoms and 1 to 3 hetero atoms selected from the group consisting of N, O and S. The nitrogen and sulfur hetero atoms may optionally be oxidized; or the nitrogen hetero atom may optionally be quaternized. The binding site is on any of the carbon atoms but with respect to $R^1a$, in the case of a hetero ring containing at least one nitrogen atom, the nitrogen atom can be the binding site.

Examples of such saturated heterocyclic group include pyrrolidinyl, piperidyl, piperidino, homopiperidyl, heptamethyleneiminyl, piperazinyl, homopiperazinyl, morpholinyl, morpholino, thioranyl, thiomorpholinyl, thiomorpholinylsufoxide, thiomorpholinylsulfone, tetrahydrofuryl, etc. Such saturated heterocyclic moieties may also be optionally substituted with 1 or 2 groups independently selected from the group consisting of: hydroxy, carboxyl, carboxyl-$C_1$–$C_8$ alkyl, aryl, aryl-$C_1$–$C_4$ alkyl, $C_1$–$C_4$ alkyl, amino, mono- or di-$C_1$–$C_4$ alkylamino, amino-$C_1$–$C_8$ alkyl, mono- or di-$C_1$–$C_4$ alkylamino-$C_1$–$C_8$ alkyl, hydroxy-$C_1$–$C_4$ alkyl, guanidino, $C_1$–$C_4$ alkylguanidino, guanidino-$C_1$–$C_8$ alkyl, $C_1$–$C_4$ alkylguanidino-$C_1$–$C_8$ alkyl, —$N(R^{11})_3A$ [wherein $R^{11}$ represents $C_1$–$C_4$ alkyl and A represents a counter ion selected from the group consisting of monovalent anions], $N(R^{11})_3A$-substituted $C_1$–$C_8$ alkyl [wherein $R^{11}$ and A have the same significances as described above], and the like.

Examples of such unsaturated heterocyclic groups include pyrrolyl, pyridyl, pyrazinyl, imidazolyl, pyrazolyl, furyl, oxazolyl, thienyl, thiazolyl, indolyl, quinolyl, isoquinolyl, etc. Such unsaturated heterocyclic group may optionally be substituted with a group selected from the group consisting of $CF_3$, $C_1$–$C_4$ alkyl, $C_1$–$C_4$ alkoxy, a halogen atom, etc.

The term "counter ion" means monovalent anion such as chloride, bromide, acetate, perchlorate, benzoate, maleate, benzenesulfonate, tartarate, hemitartarate, etc.

The term "nitrogen-containing saturated heterocyclic group" means a saturated 3- to 8-membered monocyclic nitrogen-containing heterocyclic group, which is composed of at least one nitrogen atom, carbon atoms and, if necessary, one hetero atom selected from the group consisting of O and S and which binding site is on the nitrogen atom. The nitrogen and sulfur hetero atoms may optionally be oxidized or the nitrogen atom may also be quaternized.

Examples of such nitrogen-containing saturated heterocyclic group include pyrrolidinyl, piperidino, homopiperidino, heptamethyleneiminyl, piperazinyl, homopiperazinyl, morpholino, thiomorpholino, thiomorpholinosulfoxide, thiomorpholinosulfone, etc. Such nitrogen-containing saturated heterocyclic groups may also be optionally substituted with 1 or 2 groups independently selected from the group consisting of: hydroxy, carboxyl, carboxyl-$C_1$–$C_8$ alkyl, aryl, aryl-$C_1$–$C_4$ alkyl, $C_1$–$C_4$ alkyl, amino, mono- or di-$C_1$–$C_4$ alkylamino, amino-$C_1$–$C_8$ alkyl, mono- or di-$C_1$–$C_4$ alkylamino-$C_1$–$C_8$ alkyl, hydroxy-$C_1$–$C_4$ alkyl, guanidino, $C_1$–$C_4$ alkylguanidino, guanidino-$C_1$–$C_8$ alkyl, $C_1$–$C_4$ alkylguanidino-$C_1$–$C_8$ alkyl, —N($R^{11}$)$_3$A [wherein $R^{11}$ and A have the same signifcances as described above], and N($R^{11}$)$_3$A-substituted $C_1$–$C_8$ alkyl [wherein $R^{11}$ and A have the same significances as described above], and the like.

The term "unsubstituted or substituted alkyl" means an branched and straight saturated aliphatic hydrocarbon group having 1 to 16 carbon atoms, i.e., $C_1$–$C_{16}$ alkyl, which is unsubstituted or may be substituted with a group selected from the group consisting of: amino, mono- or di-$C_1$–$C_4$ alkylamino, hydroxy, —$CO_2H$, guanidino, $C_1$–$C_4$ alkylguanidino, aryl, $C_1$–$C_4$ alkoxy, a halogen atom, —N($R^{11}$)$_3$A [wherein $R^{11}$ and A have the same significances as described above], —$CONR^2R^3$ [wherein $R^2$ and $R^3$ have the same significances as described above] and a heterocyclic group [in the case of a heterocyclic group containing at least one nitrogen atom, the nitrogen atom can be the binding site].

The neurotrophic peptide precursor polypeptide of the present invention includes the precursor polypeptides derived from both human and rat. As the rat-derived polypeptide, the precursor polypeptide having an amino acid sequence shown by SEQ ID NO: 4 is illustrated and, as the human-derived one, the precursor polypeptide having an amino acid sequence shown by SEQ ID NO: 15 is illustrated.

In the specification, amino acids, protective groups, active groups, solvents and the like are sometimes referred to by their abbreviations based on IUPAC-IUB and abbreviations conventionally used in the art.

The abbreviations for amino acid residues or amino acid derivatives are shown below.

| Abbreviations | Name |
| --- | --- |
| Asp | Aspartic acid |
| Gly | Glycine |
| Lys | Lysine |
| Leu | Leucine |
| Pro | Proline |
| Ser | Serine |
| Val | Valine |
| Trp | Tryptophan |
| Asx | Asparagine or Aspartic acid |
| Glx | Glutamine or Glutamic acid |

Unless otherwise indicated, the amino acid residues given without the prefix "L" in the specification correspond to the naturally occurring absolute configuration L.

Other abbreviations are shown below.

| Abbreviations | Name |
| --- | --- |
| Boc | t-Butyloxycarbonyl |
| OcHex | Cyclohexyl ester |
| Bzl | Benzyl |
| DCC | Dicyclohexylcarbodiimide |
| DMF | Dimethylformamide |
| TFA | Trifluoroacetic acid |
| TEA | Triethylamine |
| HOBt | 1-Hydroxybenzotriazole |
| PTC | Phenylthiocarbamyl |

The pharmaceutically acceptable salts of the human-derived neurotrophic peptide of the present invention or derivatives thereof include conventional non-toxic salts of these peptides and quaternary salts thereof. These salts may be formed from inorganic or organic acids or bases. Examples of such acid addition salts are salts of acetic acid, butyric acid, citric acid, lactic acid, tartaric acid, oxalic acid, maleic acid, succinic acid, fumaric acid, hydrochloric acid, hydrobromic acid and sulfuric acid. Salts of bases are ammonium salts, alkali metal salts such as sodium and potassium salts, alkaline earth metal salts such as calcium and magnesium salts, salts with amino acids such as arginine, lysine, etc. Such salts can be readily produced by known methods. For example, in the case of acetates, the acetates can be prepared by dissolving the neurotrophic peptide derivatives or derivatives thereof in water and adding a necessary amount of acetic acid to the solution.

[Methods for Preparation]

The neurotrophic peptide derivatives of the present invention or derivatives thereof can be synthesized in a manner similar to methods conventionally used in ordinary peptide chemistry. Such known methods are described in References 61, 62, 63, 64, 65, etc. That is, the peptide can be synthesized by selecting any of the liquid phase method and the solid phase method, depending upon the structure of the C-terminus. In more detail, where peptides contain a partial structure of —COOH or —$CONH_2$ at the C-terminus, the peptides can be obtained by any of the liquid phase method and the solid phase method but in other cases, the liquid phase method is rather preferred.

For example, in the case that the peptide derivative is synthesized by the solid phase method, the C-terminal amino acid (amino group-protected amino acid) or the C-terminal substituent (the substituent having carboxyl group; in the case that an amino group is contained, the amino group is protected) is bound to insoluble carrier through the carboxyl group. If necessary and desired, after the amino protective group is removed, the amino group-protected amino acids or the amino acid derivatives (in the case that a free amino group is present, the amino group is protected) are successively coupled, according to the amino acid sequence of the desired peptide, through condensation of the reactive carboxyl groups with the reactive amino groups or with the reactive hydroxy groups. The synthesis is carried out step by step. After synthesis of the whole sequence, if necessary, the N-terminal substituent is condensed. Then, the peptide is withdrawn from the insoluble carrier and at the same time, the protective group is removed. Further if necessary and desired, the N-terminal substituent or C-terminal substituent is condensed and the protective group is removed to obtain the desired peptide.

In the case of synthesis by the liquid phase method, the C-terminal amino acid having a free amino group at the terminal (carboxyl group-protected amino acid) or the C-terminal substituent (the substituent having free amino or hydroxy group; in the case that a carboxyl group is present, the carboxyl group is protected) is successively coupled by the amino group-protected amino acid according to the amino acid sequence of the desired peptide, through condensation of the reactive amino groups or the reactive hydroxy groups with the reactive carboxyl groups. If necessary, the N-terminal substituent is finally condensed-therewith. Thus, the whole sequence can be synthesized. The whole sequence may also be synthesized by synthesizing in a similar manner, removing the selected protective groups and coupling the resulting peptide fragments to each other. The protective group is removed and if necessary, the N-terminal substituent or the C-terminal substituent is condensed and the protective group is removed to obtain the desired peptide.

In the methods described above, the reactive functional groups are preferably protected.

Examples of the protective group of the amino group include benzyloxycarbonyl, t-butyloxycarbonyl, p-methoxybenzyloxycarbonyl, 2-chlorobenzyloxycarbonyl, p-toluenesulfonyl, trifluoroacetyl, phthalyl, formyl, o-nitrophenylsulfenyl, 3-nitro-2-pyridinesulfenyl, diphenylphosphinothioyl, etc.

Examples of the protective group of the carboxyl group include alkyl esters (esters of $C_1$–$C_4$ such as methyl, ethyl, t-butyl, etc.), benzyl ester, p-nitrobenzyl ester, p-methylbenzyl ester, cyclohexyl ester, cyclopentyl ester, etc.

The hydroxy group in Ser, Tyr, etc. may not be necessarily protected but if necessary, can be protected with benzyl, 2,6-dichlorobenzyl, t-butyl, benzyloxycarbonyl, acetyl, etc. The indolyl group in Trp, etc. may be protected, if necessary, with formyl, benzyloxycarbonyl, 2,4-dichlorobenzyloxycarbonyl, etc. The guanidino group may also function to be protected in the state protonated with hydrochloric acid, etc. but, if necessary, may also be protected with p-toluenesulfonyl, nitro, benzyloxycarbonyl, p-methoxybenzenesulfonyl, mesitylene-2-sulfonyl, etc.

In the methods described above, peptide bonds can be formed by known methods, for example, the method using condensing agents of carbodiimide type such as dicyclohexylcarbodiimide, 1-ethyl-3-(3-dimethylaminopropyl)carbodiimide, etc.; the symmetrical acid anhydride method, the mixed acid anhydride method, the azide method, the activated ester method, the oxidation-reduction method, the diphenylphosphoryl azide method, the method using carbodiimide type condensing agent and additives (1-hydroxybenzotriazole, N-hydroxysuccinimide, etc.).

For removing the protective group, there are known, for example, the trifluoroacetic acid method, the methanesulfonic acid method, the trifluoromethanesulfonic acid method, the hydrogen fluoride method, the liquid ammonia-sodium method, the catalytic reduction method, the alkali saponification method, etc.

The peptides produced by the present invention can be purified by using known methods conventionally used in the art of peptide chemistry, singly or in combination, such as ion exchange chromatography, partition chromatography, gel chromatography, reverse phase liquid chromatography, etc.

[Pharmacological Activities]

The human-derived neurotrophic peptide or its derivatives of the present invention can regulate differentiation and maturation of neuronal cells. That is, the neurotrophic peptide and derivatives thereof accelerate the acetylcholine synthesis in the tissue of medial septum nuclei. The biological activity can be determined by the method of Ojika, K., et a. (Reference 66).

1. Methods of Tissue Culturing

Medial septal nucleus was extracted from the brains of 16-day-old SD rat embryos and microscopically dissected into small pieces. A few dozen pieces of tissue explant were inoculated onto poly-L-Lysine-coated 35 mm plastic dishes. The culture was maintained with modified $N_2$ defined medium according to Bottenstein et al and incubated under conditions of 7% $CO_2$ mixed air and 36° C. Co-culture was carried out by mechanically dissociating the hippocampal tissue therefrom, and subjecting it to low-speed centrifugation to provide $1\times10^5$ cells spun down, which were in turn cultured together with 30 pieces of the septal tissue in a culture medium containing 1% calf serum. The medium was changed every 3 days.

2. Method for Biochemical Measurement of Activity

Except in the experiment for the study of sequential growth, the cultured tissue on the 9th day was washed with a Tris-HCl (pH 7.4) buffered Tyrode's solution, followed by preincubation in a high-K (55 mM KCl) Tyrode's solution, and then incubation in a Tyrode's solution containing $^3$H-choline chloride at 37° C. for 30 minutes. After washing off the free $^3$H-choline, the tissue was dissolved in a formic acid/acetone solution, and a small amount thereof was used to determine the choline uptake of the cultured tissue, while the $^3$H-choline in the remaining portion was converted to phosphocholine with choline kinase, after which the $^3$H-acetylcholine (Ach) was extracted with TPB (tetraphenyl boron) to determine the Ach-productivity of the cultured tissue. The choline uptake and Ach-productivity were expressed as amounts per one piece of cultured tissue. Choline acetyl-transferase (CATase) was measured using $^{14}$C-acetyl-CoA, according to the method of Fonnum, biochemical Journal, 115, 465–472 (1969).

[Application to Therapeutic Compositions]

The human-derived neurotrophic peptide or its derivatives of the present invention are useful for the treatment of neurological degenerative disorders and dementia. The neurological degenerative disorder is a disease caused by degeneration/denervation of cholinergic neuron and is exemplified by Alzheimer syndrome, Alzheimer type dementia, amyotrophic lateral sclerosis, Parkinson's disease, etc.

As dementia, there are Alzheimer type dementia, parkinson's dementia, cerebro-vascular dementia.

Animal to which the neurotrophic peptide derivatives of the present invention are applicable is not limited.

The compounds of the present invention can be applied to human beings as well as to other various species of mammals such as mouse, rat, dog, calf, horse, goat, sheep, rabbit, hog, etc.

The neurotrophic peptide or its derivatives of the present invention can be administered to these animals and human by ordinary route, for example, orally, intramuscularly, intravenously, subcutaneously, intraperitoneally, pernasally and intracerebrally. Dose and time of administration vary depending upon animal species, administration route, condition of disease, body weight, etc. In human, the peptides or its derivatives can be administered to adult in a daily dose of approximately 1 μg to 1 g, once or in several portions. Examples of pharmaceutical preparations include powders, granulates, granules, tablets, capsules, suppositories, injections, nasal preparations, etc. The pharmaceutical preparations can be prepared in a conventional manner, using conventional carriers for preparations. That is, in the case of preparing oral preparations, excipients or carriers are added to the active ingredient and if necessary, binders, disintegrators, lubricants and coloring agents, are further added thereto and then prepared into tablets, granules, powders, capsules, etc., by known methods. In the case of preparing injections, pH regulators, buffers, stabilizers, solubilizing agents, etc. are added depending upon necessity and prepared into injections in a conventional manner.

Hereafter the present invention is described in more detail by referring to the examples below but is not deemed to be limited thereto.

EXAMPLE 1

Preparation of Rabbit Polyclonal Antibody to Rat Hippocampal Neurotrophic Peptide Rabbit polyclonal antibodies to rat HCNP having amino acid sequence shown by SEQ ID NO: 2 was prepared. The procedures are described below (Reference 67).

In 2 ml of 0.1M ammonium acetate (pH 7.0) were dissolved 3 mg of synthetic oligopeptide having an amino acid sequence shown by SEQ ID NO: 2 and 10 mg of bovine serum albumin and, 1.3 ml of 0.02M glutaraldehyde was added to the solution. The solution was stirred at room temperature for 5 hours. After dialysis to $H_2O$ overnight, the solution was lyophilized to recover about 10 mg of complex protein.

After 1.5 mg of the complex protein was dissolved in 1.5 ml of physiological saline, 1.5 ml of Freund's complete adjuvant was added to the solution to form an emulsion.

3 rabbits were boostered with adjuvant containing 0.25 to 0.5 mg/rabbit of the complex protein. Sensitization was performed by scattering the adjuvant beneath the back skin at about 50 points per skin (10 cm×10 cm) and repeating the booster every 2 2 other weeks. Ten days after the booster 5 times in total, blood was collected from carotid artery and allowed to stand at 4° C. overnight to precipitate blood clot. By centrifugation at 3000 rpm, the supernatant was recovered to make antibody solution. The antibodies obtained from the 3 rabbits were made Ab-1, Ab-2 and Ab-3, respectively. The antibodies all had similar titers (cf., Example 3).

EXAMPLE 2

Preparation of Probe

Based on the sequence of 6 amino acids shown by Asp-Ile-Ser-Gln-Trp-Ala at the central portion out of the amino acid sequence of rat HCNP composed of 11 amino acids, 17 continuous oligonuleotides were synthesized (FIG. 1). The synthesis was performed to design 24 combinations in probe by classifying into 3 probes at the Ser site, respectively. In the sequences shown in FIG. 1, the nucleotide at the 6-position from the 5' end of the probe indicates a mixture of dT and dC in equimolar amounts.

Next, in order to synthesize the probe at the C terminus in the amino acid sequence of rat HCNP described above, 16 continuous oligonucleotides were synthesized based on 6 amino acid sequence shown by Gln-Trp-Ala-Gly-Pro-Leu at the C terminus. As the probe at the C terminus, one probe in 256 different combinations was synthesized (FIG. 1).

The nuecleotide sequences of the probe shown in FIG. 1 have reverse sequences of the nucleotide sequence deduced from the amino acid sequence. Any of the oligonucleotides were synthesized using DNA Synthesizer (Model 381) manufactured by Applied Biosystems Co. The synthesized DNAs were purified using OPC Cartridge (manufactured by Applied Biosystems Co.).

Labeling of the oligonucleotides with $^{32}P$ was performed as follows: To 10 μl of a reaction composition of 67 mM Tris-HCl (pH 8.0), 17 mM β-mercaptoethanol and 10 mM $MgCl_2$ were added 1 μg of the synthetic oligonucleotide, 50 μCi of [γ-$^{32}$P] ATP (manufactured by Amersham Co., PB10218, 10 mCi/ml, 5000 Ci/mmol) and 10 units of T4 polynucleotide kinase followed by incubation at 37° C. for 30 minutes. Thereafter heating was performed at 65° C. for 10 minutes to terminate the reaction. Gel filtration was performed using PD-10 column manufactured by Pharmacia Fine Chemicals, Inc. which had been equilibrated with TE solution (10 mM Tris-HCl (pH 7.5), 1 mM EDTA) to remove an excess of the nucleotide. Specific activity of the probe was approximately $2 \times 10^7$ cpm/μg.

EXAMPLE 3

Purification and Detection of Precursor Protein of Rat HCNP

As shown in Example 1, 3 antibodies composed of 11 amino acids to rat HCNP were prepared. Proteins reactive with these antibodies was detected by Western blotting.

Ice-cooled PBS (pH 7.2) solution was added to rat brain and homogenized. After centrifugation at 10000×g for 30 minutes, the supernatant was collected and subjected to 14% or 16% SDS-polyacrylamide gel electrophoresis (Reference 68). The protein electrophoresed to Immobilon PVDF Filter (manufactured by Millipore Co., Ltd.) was electrically transferred (Reference 69). The transfer was carried out under conditions of applying 70 V for 4 hours using a buffer solution for blotting composed of 25 mM Tris-HCl (pH 8.3), 192 mM glycine, 0.02% SDS/methanol (80/20). The filter was washed with TBS (20 mM Tris-HCl (pH 7.5), 150 mM NaCl) and incubated at room temperature for an hour in 3% gelatin-TBS solution to block with gelatin the membrane surface not adsorbed with the protein. After shaking and washing with TBS, primary antibody (500-fold dilution) diluted with 1% gelatin-TBS was reacted with the protein adsorbed onto the filter for 4 hours followed by shaking with T-TBS (0.05% Tween 20, TBS) for 3 times 5 minutes each.

The filter was put in 1% gelatin-TBS solution containing peroxidase-labeled secondary antibody (manufactured by Amersham Co.) diluted to 2000-fold and incubated at room temperature for 2 hours. The filter was washed with T-TBS for 10 minutes 3 times. Lastly, 60 mg of 4-chloro-1-naphthol was dissolved in 20 ml of methanol and the resulting solution was mixed with 100 ml of TBS solution. The membrane was dipped in a peroxidase color-forming solution to which $H_2O_2$ was added in a concentration of 0.01% to form a color (Reference 70). As the result, the protein having a molecular weight of 23 kilodaltons present in the rat brain was reacted with the antibody to rat HCNP.

In the three polyclonal antibodies shown in Example 1, the protein could be detected with a similar dilution in any case.

In order to determine the amino acid sequence of the protein, ice-cooled PBS (pH 7.2) was added to the brains collected from 20 rats. After homogenization, 20 ml out of 33 ml of the supernatant was subjected to gel filtration with 20 mM HEPES buffer (pH 7.2) using Sephadex G-150 Fine Column (diameter of 6 cm×84 cm). By Western blotting through SDS-polyacrylamide gel electrophoresis, the fraction of 50 ml reactive with the antibody was collected. Ten milliters of the fraction were applied to high performance liquid chromatography to purify the protein. Using a column of RP-304 (diameter of 4.6 mm×250 mm) manufactured by BioRad Co., chromatography was carried out with the solvent system of 0.1% trifluoroacetic acid (TFA)-acetonitrile, whereby the desired protein was eluted in an acetonitrile concentration of approximately 38 to 40%.

EXAMPLE 4

Construction of Rat Hippocampal cDNA Library

I) Preparation of mRNA mRNA was isolated from the hippocampal tissue (rat hippocampus collected from 30 rats; wet weight of about 2 g) withdrawn from neonatal rats basically in a conventional manner. Using a homogenizer, 2 mg of the frozen tissue was immediately homogenized at room temperature in the presence of 4M guanidine solution (4M guanidine thiocyanate, 100 mM Tris-HCl (pH 7.5), 1% β-mercaptoethanol). Thereafter, in order to physically destroy high molecular chromosomal DNA, injection and ejection were repeated 10 times using a syringe equipped with a 18 G needle. To the thus treated suspension was added 10% sodium sarcosylsulfate solution in a final concentration of 0.5%. After centrifugation at room temperature and 2000 rpm for 5 minutes, the supernatant was collected and the cell debris was removed therefrom. Onto 1 ml of 5.7M cesium chloride and 4 mM EDTA in a polyallomer tube was gently overlaid 3 ml of the guanidine solution described above. After centrifugation at 45000 rpm for 11 hour at 20° C., the pellet was dissolved in 10 mM Tris-HCl (pH 7.5), 5 mM EDTA and 1% SDS. After ¹/₁₀ volume of 3M sodium acetate was added to RNA solution, 2.2-fold volume of ethanol was added thereto to precipitate the total RNA at −20° C. By ethanol precipitation several times, about 2 mg of the total RNA was obtained.

Poly(A) mRNA was purified from the total RNA as follows, using oligo (dT) cellulose column. In 2 ml of TE solution was dissolved 1.5 mg of the total RNA purified by the ethanol precipitation described above. After heating at 70° C. for 5 minutes, the solution was chilled and ⅕ volume of 10 mM Tris-HCl (pH 7.4), 1 mM EDTA and 3M NaCl was added to the solution. The mixture was laid over oligo (dT) cellulose column (5 ml; manufactured by Pharmacia Fine Chemicals, Inc., oligo (dT) cellulose Type 7). A sample was applied to the column under specific gravity to collect poly(A) mRNA molecule on the cellulose column, trapping mRNA containing poly(A) tail onto oligo (dT). The solution passed through the column was again heated, chilled and applied to the same column. After the column was washed with 10-fold volume of 10 mM Tris-HCl (pH 7.4), 1 mM EDTA and 0.5M NaCl, the column was further washed with 6-fold volume of 10 mM Tris-HCl (pH 7.4), 1 mM EDTA and 0.1M NaCl. Then poly(A) mRNA was eluted with TE solution kept at 70° C. The eluate was again heated at 70° C. for 10 minutes and subjected to second chromatography using oligo (dT) cellulose column (2 ml) in a similar manner. The amount of poly(A) mRNA finally obtained was 103 µg.

II) Preparation of Rat Hippocampal Tissue-Derived cDNA Library

To prepare cDNA from the thus purified poly(A) mRNA, cDNA was synthesized using oligo (dT) primer and random primer. Some differences are noted between the respective methods for synthesis of single stranded cDNA using two kinds of primers. Therefore, the respective methods are described below in detail.

(1) Synthesis of Single Stranded cDNA using Oligo (dT) Primer

To the synthesis of cDNA using oligo (dT) primer, the following procedures were carried out. The thus prepared rat hippocampal tissue-derived poly(A) mRNA, 8 µg, was dissolved in 20 µl of $H_2O$ in which RNase was inactivated by diethyl pyrocarbonate treatment. After heating at 70° C. for 10 minutes, the solution was cooled on ice.

Then 10 µl of 5×RT buffer (250 mM Tris-HCl (pH 7.5), 375 mM KCl, 15 mM $MgCl_2$) was added to the solution. Furthermore, 4 µl of human placenta ribonuclease inhibitor (20 units/µl, manufactured by Amersham Co.), 1.5 µl of nucleotide solution (solution containing 10 mM each f dATP, dGTP, dTTP and dCTP), 50 µCi (5 µl) of [α-$^{32}$P] dCTP (manufactured by Amersham Co., PB10205, 10 mCi/ml, 3000 Ci/mmol) and 1 µl of 250 mM dithiothreitol were added to the mixture and the volume was finally made 49 µl with $H_2O$. Lastly, 1 µl of reverse transcriptase (derived from Mo-MLV, 200 units/µl, manufactured by Besesda Research Laboratories) was added to the reaction mixture. After heating at 37° C. for an hour, the reaction tube was put back on ice to complete the synthesis of single stranded cDNA.

(2) Synthesis of Single Stranded cDNA Using Random Primer

After a solution of 8 µg of poly(A) mRNA dissolved in 8 µl of $H_2O$ heat-treated in a manner similar to the case using oligo (dT) primer described above, 16 µl of 5×First Strand Buffer (250 mM Tris-HCl (pH 8.3), 50 mM $MgCl_2$, 50 mM dithiothreitol), 4 µl of 80 mM sodium pyrophosphate solution, 4 µl of human placenta ribonuclease inhibitor (20 units/µl, manufactured by Amersham Co.), 5 µl of deoxynucleotide triphosphate mixture solution containing 10 mM each of dATP, dGTP, dTTP and dCTP, 4 µl of random hexanucleotide primer of 0.02 OD/µl and 50 µCi (5 µl) of [α-$^{32}$P] dCTP (manufactured by Amersham Co., PB10205, 10 mCi/ml, 3000 Ci/mmol) was added to the heat-treated solution. The volume was finally made 72 µl with $H_2O$. Lastly, 8 µl of reverse transcriptase (derived from AMV, 20 units/µl, manufactured by Amersham Co.) was added to the reaction mixture. After heating at 42° C. for an hour, the reaction tube was put back on ice to complete the synthesis of single stranded cDNA.

(3) Synthesis of Double Stranded cDNA

To the thus synthesized single stranded cDNA were added a buffer solution and enzymes in 20 mM Tris-HCl (pH 7.5), 5 mM $MgCl_2$, 10 mM $(NH_4)_2SO_4$, 100 mM KCl, 0.15 mM β-NAD, 50 mM BSA, 40 µM dNTP, 8.5 units/ml E. coli ribonuclease H and 230 units/ml E. coli DNA polymerase I. The mixture was reacted at 12° C. for 60 minutes and then at 22° C. for 60 minutes. In order to inactivate the enzymes added, the reaction mixture was heated at 70° C. for further 10 minutes and put back onto ice. To the reaction solution were added 2 units of E. coli DNA polymerase I Klenow fragment. After reacting at 37° C. for 30 minutes, 16 units of T4 DNA polymerase were added to the mixture. By reacting at 37° C. for 15 minutes, the both termini of double stranded cDNA were rendered blunt. The reaction was terminated by adding 4 µl of 0.25M EDTA (pH 7.5) per 100 µl of the reaction solution. The synthesis rate of double stranded cDNA synthesized from the used mRNA was 30% and 65%, respectively, in the cases of using oligo (dT) primer and random primer. Next, the synthesized cDNA was purified using a Qiagen column manufactured by DIAGEN Co.

The purification of DNA using Qiagen column was performed as follows. The cDNA solution previously adjusted to a concentration of 0.5M NaCl and 50 mM MOPS (pH 7.0) was applied to Qiagen column equilibrated with 0.5M NaCl, 50 mM MOPS (pH 7.0) and 15% ethanol. The column was washed with 1.0M NaCl, 50 mM MOPS (pH 7.0) and 15% ethanol in a volume more than 10 times excess that of the column and then eluted with 1.5M NaCl, 50 mM MOPS (pH 7.5) and 15% ethanol. In order to completely remove the resin packed from the elute, phenol-chloroform treatment and chloroform treatment were performed. Then 0.8-fold volume of isopropanol was added to the system. After allowing to stand in ice water for 15 minutes, centrifugation was performed at 15000 rpm for 30 minutes. The thus obtained pellet was dissolved in 0.3M sodium acetate solution and then 2.5-fold volume of ethanol was added to the solution. The mixture was allowed to stand at −80° C. for 15 minutes. Then, the mixture was centrifuged at 15000 rpm for 10 minutes to recover DNA.

An excess amount of EcoRI adaptor (manufactured by Pharmacia Fine Chemicals, Inc. and Takara Shuzo Co., Ltd.) was ligated with the purified double stranded cDNA, which termini were rendered blunt in 100 μl of the reaction solution containing 20 mM Tris-HCl (pH 7.6), 6.7 mM dithiothreitol, 6.7 mM $MgCl_2$, 1 mM ATP and 500 units/ml T4 DNA ligase. Next, in order to remove the excess EcoRI adaptor, purification was performed again using Qiagen column followed by phosphorylation of EcoRI adaptor at 5' end with 67 mM Tris-HCl (pH 8.0), 17 mM β-mercaptoethanol, 10 mM $MgCl_2$, 1 mM ATP and 200 units/ml of T4 DNA polynucleotide kinase.

In order to remove an excess of ATP and further remove synthetic cDNA having a short size from the thus obtained DNA, Qiagen column was again used. The procedure was performed in the same manner described above except for washing the column with 1.3M NaCl, 50 mM MOPS (pH 7.0) and 15% ethanol. Under the conditions for washing, it is possible to remove excess ATP and cDNA having a size shorter than about 700 bp in length.

The thus purified cDNA was further purified and concentrated by phenol-chloroform treatment and ethanol precipitation to prepare the final cDNA library. The amounts of cDNA obtained using oligo (dT) primer and random primer were finally 2 μg and 1.3 μg, respectively.

EXAMPLE 5

Screening

I) Ligation of Double Stranded cDNA and λgt11 Vector DNA

In order to insert the double stranded cDNA added with EcoRI adaptor as described above into EcoRI cleavage site of λgt11, ligation was performed with T4 DNA ligase. The ligation was carried out under the following conditions.

After previously digesting with EcoRI, the phosphate group at 5' end was removed from λgt11 vector DNA with *E. coli* alkaline phosphatase. The λgt11 vector DNA (2 μg; 66 fmol) was mixed with double stranded cDNA (160 ng; about 100 fmol). The mixture was reacted at 12° C. overnight with a reaction composition (final volume: 10 μl) containing 20 mM Tris-HCl (pH 7.6), 6.7 mM $MgCl_2$, 6.7 mM dithiothreitol, 1 mM ATP and 5 units of T4 DNA ligase.

II) In Vitro Packaging

Using In Vitro Packaging Kit (GIGAPACK II GOLD) manufactured by Stratagene Co., ⅓ of the recombinant DNA obtained as described above was packed to obtain phage particles. The number of transformants obtained using these phage particles was $8.8 \times 10^7$ plaque forming units (pfu) and $2.5 \times 10^7$ pfu, respectively, per 1 μg of cDNA synthesized using oligo (dT) primer and random primer.

III) Screening of λgt11 Phage Library by Polyclonal Antibody to Rat HCNP

The phage library containing cDNA described above was infected using *E. coli* Y1090 as host and cDNA clones synthesized using oligo (dT) primer and random primer were inoculated, respectively, on 10 plats of agar medium having a dimeter of 150 mm so as to form $1 \times 10^6$ plaques. Each plate was cultured at 42° C. for 2 hours and then at 370° C. for 1.5 hour. Next, a nitrocellulose membrane filter (BA85; manufactured by Scheicher And Schuell Co., Ltd.) previously treated with 20 mM isopropyl-β-D-thiogalactopyranoside was put on agar medium inoculated with the transformants and cultured at 37° C. for further 3.5 hours. The filter was gently peeled off from the agar medium and washed 5 times with T-TBS solution (60 mM Tris-HCl (pH 7.5), 150 mM NaCl, 0.05% Tween-20) for 5 minutes. Then the filter was transfered to TBS-1% BSA solution (60 mM Tris-HCl (pH 7.5), 150 mM NaCl, 1% bovine serum albumin) and mildly shaken at room temperature for 3 hours to adhere bovine serum albumin to the filter, for the purpose of reducing the background density when reacted with the antibody.

Next, the filter is put in TBS-1% BSA solution containing polyclonal antibody (Ab-1) to rat HCNP (SEQ ID NO: 2) of 500-fold dilution, which was gently shaken at room temperature overnight thereby to react the primary antibody with the protein immobilized to the filter. The filter was washed 3 times for 5 minutes and put in TBS-1% BSA solution containing 200-fold diluted biotinylated anti-rabbit Ig donkey antibody (manufactured by Amersham Co.). The secondary antibody was reacted at room temperature for 2 hours with the primary antibody bound to the protein immobilized onto the filter. After washing 3 times with T-TBS for 5 minutes, the filter was put in TBS-1% BSA solution containing 200-fold diluted streptoavidin-biotinylated peroxydase complex (manufactured by Amersham Co.) followed by reacting at room temperature for an hour. The peroxidase complex bound to the secondary antibody was detected by dipping the filter at room temperature for 30 minutes in 200 ml of TBS solution (60 mM Tris-HCl (pH 7.5), 150 mM NaCl) added with 40 ml of 3 mg/ml 4-chloro-1-naphthol, 1 ml of $H_2O_2$ and 1 ml of 1M imidazole, whereby a color was formed. As the result of screening using the antibody, 12 and 1 positive clones were obtained, respectively, from the cDNA libraries synthesized using oligo (dT) primer and random primer.

Each clone was monocloned using the same primary antibody (Ab-1) as described above according to the same detection procedure. In order to elucidate the reactivity with the 3 polyclonal antibodies shown in Example 1, each of the monocloned clones was appropriately diluted to form several ten plaques per μl, and 1 μl of the dilution of each clone was spotted onto 3 plates. The reactivity of the protein produced from each clone with the 3 antibodies was examined using the same detection system as described above. As the result, the proteins derived from the 3 clones reacted significantly with the 3 antibodies. Among these clones, two (A61, A62) and one (R4) were obtained from the cDNA library synthesized using oligo (dT) primer and random primer, respectively.

IV) Screening of λgt11 Phage Library by Oligonucleotide Probe Prepared from the Nucleotide Sequence Deduced from the Amino Acid Sequence of Rat HCNP In order to elucidate if the nucleotide sequence of SEQ ID NO: 1 deduced from rat HCNP is contained in the inserted cDNA sequence contained each of the monoclones described above, plaque hybridization was performed using oligonucleotide probe (Reference 10). The two oligonucleotide probes shown in FIG. 1 were labeled by the method shown in Example 2, using $^{32}P$. The labeled probes were diluted with hybridization solution having the composition of 20 ml of 6×SSC (0.9M NaCl, 0.09M sodium citrate), 5×Denhardt (0.1% Ficol, 0.1% polyvinylpyrrolidone, 0.1% bovine serum albumin) and 0.1% SDS to prepare $1\times10^6$ cpm/ml of probe solution.

Using *E. coli* Y1088 as host, 1 µl of the phage dilution was spotted to form several ten plaques per each of 13 clones in total selected using antibody (Ab-1) as described in III above followed by culturing at 42° C. for 2 hours and then at 37° C. for 4 hours. Thereafter the phase was transferred to a nitrocellulose membrane filter. The filter was treated for 5 minutes with 0.5N NaOH and 1.5M NaCl solution to denature DNA, and then treated with 1M Tris-HCl (pH 7.5) and 3M NaCl for 10 minutes to immobilize DNA onto the filter. After washing with 2×SSC (0.3M NaCl, 0.03M sodium citrate) for 5 minutes, the filter was baked at 80° C. for 2 hours.

The filter was again wetted with 2×SSC and prehybridization was carried out at 34° C. for 6 hours with probe-free hybridization solution. Then hybridization was continued overnight at 34° C. with the probe solution described above.

The filter was washed with 2×SSC and 0.1% SDS at room temperature for 15 minutes and then 4 times with 2×SSC and 0.1% SDS at 42° C. for 30 minutes. Thereafter clones having homology to the two probes were detected by autoradiography.

The results reveal that only the 3 clones (A61, A62, R4) which showed the same reactivity as that of the 3 polyclonal antibody shown in III) above contained the region having homology to the two oligonucleotide probes.

EXAMPLE 6

Determination of Nucleotide Sequence of Gene Encoding the Precursor Protein Containing Rat HCNP:

Phage DNA was prepared from the 3 clones (A61, A62, R4) which would be able to encode the precursor protein of rat HCNP obtained in Example 5 described above. The inserted DNA fragment was then subcloned and the nucleotide sequence was determined.

The phage DNA was prepared according to the following procedures. The unified phage clone was inoculated to apear on the entire surface of plate. After culturing at 37° C. overnight, 5 ml of λ diluent (10 mM Tris-HCl (pH 7.5), 10 mM MgCl$_2$, 0.1 mM EDTA) was poured onto agar medium to perform plate lysate thereby to amplify the phage particles. Using the thus obtained phage particles, the phage was prepared in large quantities by liquid culture. After 2 ml of *E. coli* Y1088 preculture and phage particles were added to 100 ml of liquid medium at multiplicity of infection (moi)=0.05, an Erlenmyer's flask was vigorously shaken until *E. coli* lyzed. After lysis, 1 ml of chloroform was added to completely lyze *E. coli*. The obtained phage solution was centrifuged at 9000 rpm for 10 minutes. After the cell debris of *E. coli* was removed, DNase I and RNase A were added to the supernatant in 10 µg/ml. The mixture was kept at 37° C. for an hour. Then, ⅕-fold amount of 30% polyethylene glycol and 3M NaCl solution was added and cooled in ice for an hour. After centrifugation at 9000 rpm for 10 minutes, the resulting pellet was suspended in 3 ml of 100 mM Tris-HCl (pH 7.5), 100 mM NaCl and 25 mM EDTA, and 3 ml of 4% SDS was added to the suspension. The mixture was heated at 70° C. for 20 minutes. Then 3 ml of 2.55M potassium acetate (pH 4.8) was added to the suspension. After stirring, centrifugation was performed at 17000 rpm for 30 minutes at 4° C. and the supernatant was passed through a glass filter to remove impurities. The filtrate was applied to Oiagen-pack 100 (manufactured by DIAGEN Co.) equilibrated with 750 mM NaCl, 50 mM MOPS (pH 7.0) and 15% ethanol. The column was then washed with 4 ml of 1.0M NaCl, 50 mM MOPS (pH 7.0) and 15% ethanol and DNA was eluted with 4 ml of 1.2M NaCl, 50 mM MOPS (pH 8.0) and 15% ethanol. After 0.8-fold volume of isopropanol was added to the eluate, the mixture was allowed to stand in ice for 15 minutes followed by centrifugation at 17000 rpm for 30 minutes. The pellet was dissolved in 0.3M sodium acetate (pH 4.5) and 2.5-fold volume of ethanol was added to the solution. After cooling at −80° C. for 15 minutes, centrifugation was performed to recover DNA.

Insert cDNA fragment prepared by digesting phage clone DNA (1 µg) with a suitable restriction enzyme and purifying was inserted into cleaved and dephosphorylated M13mp19 or M13mp18 phage vector. The restriction enzyme map of clone A61DNA having the longest insert cDNA among clones A61, A62 and R4 and strategy for determining the nucleotide sequence are shown in FIG. 2. The nucleotide sequence was determined by preparing single stranded phage DNA from the transformant having insert cDNA fragment of clone A61 by DNA Sequencing Kit (manufactured by United States Biochemicals Co., Sequenase Version 2.0).

The thus determined nucleotide sequence of clone A61 had one large open reading frame. The open reading frame contained in this cDNA insert was composed of 186 amino acids from 5' end of cDNA, while ATG sequence which would act as a translation initiation sequence of eukaryote was missing. Poly(A) sequence present at 3' end of mRNA was found at the 3' end of this cDNA and the same sequence as AATAAA sequence, poly(A) additional signal of 6 nucleotides generally found in most mRNAs of eukaryote, was located at the upstream. The DNA sequence of cDNA insert thus determined and the open reading frame are shown in FIGS. 3A and 3B, respectively.

The amino acid sequence encoded by this cDNA can be deduced as shown in FIG. 4. The polypetide is composed of 186 amino acids and its molecular weight was determined to be 20669.1 daltons. In rat, rat HCNP of SEQ ID NO: 2 showing a neurotrophic activity is located in the region from the first amino acid residue to the eleventh amino acid residue, at the N terminus of the polypeptide shown in FIG. 4. The nucleotide sequence corresponding to the amino acid region is shown by SEQ ID NO: 1. The cDNA insert of clone A62 contained the downstream region from the second amino acid residue in the amino acid sequence shown in FIG. 4. On the other hand, the same amino acid terminus as that of A61 was detected in clone R4.

EXAMPLE 7

Selection of Clone Having the Full Length cDNA and Determination of Nucleotide Sequence of Insert DNA Fragment The A61 clone cDNA described above was not extended to the translation initiation codon so that the N terminus inherent to the polypeptide could not be analyzed. Therefore, Hinc II-Hinc II fragment of about 190 bp shown in the restriction enzyme map of FIG. 2 was labeled with $^{32}$P by Random Prime Labeling Kit (manufactured by Amersham Co.). Using the thus labeled fragment as a probe, cDNA clones extended to the 5' upstream region of the translation intiation codon were selected and nucleotide sequences were determined.

Using *E. coli* Y1088 as host, λgt11 phage library incorporated with cDNA synthesized by using oligo (dT) primer was subjected to plating on 10 plates (150,000 pfu per agar medium having a diameter of 150 mm). The phage DNA was immobilized onto a nitro cellulose membrane filter in the same manner as in Example 5 and prehybridization was carried out at 42° C. for 6 hours with hybridization solution having a composition of 50% formamide, 6×SSC, 5×Denhardt solution and 0.1% SDS. Then hybridization was continued overnight at 42° C. with hybridization solution (1×10⁶ cpm) containing the labeled Hinc II-Hinc II fragment described above.

The filter was washed with 2×SSC and 0.1% SDS at room temperature for 15 minutes and then 3 times for 30 minutes. Thereafter clones were selected by autoradiography. The resulting 9 clones were isolated by second and third screenings to obtain phage solution.

For the purpose of selecting cDNA clones further extended to the 5' end of mRNA from the selected clones were again rescreened using as a probe DNA fragment of about 90 bp from the EcoRI adaptor sequence to the Hinc II digestion site shown in the restriction enzyme map of A61 clone cDNA in FIG. 2.

The phage solution was spotted on agar medium in such a way that several tens of plaques per each clone would appear, and hybridization was performed according to the screening procedures described above. The results reveal that 6 out of 9 clones are clones bearing cDNA extended at least to the upstream of the 5' end Hinc II cleavage site shown in the restriction enzyme map of FIG. 2. DNA of these 6 λ phase clones was prepared by the liquid culture described in Example 6. After digesting with EcoRI, inserted DNA was subcloned to the EcoRI site of M13mp19 previously treated with alkaline phosphatase to determine the nucleotide sequence. As the result, as shown in SEQ ID NO: 3, ATG sequence which is translation initiation codon was present in the nucleotide sequence of cDNA insert contained in clone AO10-12, just before rat HCNP sequence having the rat hippocampus-derived neurotrophic factor activity. The results of deducing the amino acid sequence encoded in cDNA of clone AO10-12 are shown in SEQ ID NO: 4. The amino acid sequence described in SEQ ID NO: 4 does not contain ATG sequence which is translation initiation codon.

Scanning of data base by cDNA indicates that the amino acid sequence of bovine phosphatidylethanolamine binding protein showed 84.4% homology to amino acid sequence encoded by DNA (Reference 9).

In AO1-1 which is one of the clones extended to the upstream of the 5' end Hinc II cleavage site in the restriction enzyme map shown in FIG. 2, 135 amino acid residue counted from methionine residue which is assumed to be translation initiation codon was lysine residue (glutamic acid residue in clones A61, R4 and AO10-12). GAG (Glu) sequence in clones A61, R4 and AO10-12 is converted to AAG (Lys) sequence in AO1-1.

EXAMPLE 8

Degradation of the Precursor Protein Containing Rat HCNP by Lysyl Endopeptidase and Amino Acid Sequence of the Constituent Peptide In order to determine the amino acid sequence of the protein having a molecular weight of 23 kilodaltons present in rat hippocampal brain showing reactivity with the antibody to rat HCNP as shown in Example 3, the oligopeptide formed by degradation by lysyl endopeptidase was purified.

The oligopeptide caused by degradation of the protein having a molecular weight of 23 kilodaltons with lysyl endopeptidase was applied to high performance liquid chromatography to isolate and purify the respective fragments. The oligopeptide was fractionated, using RP-304 Column (diameter of 4.6 mm×250 mm; manufactured by Biorad Co.) by the solvent system of 0.1% trifluoroacetic acid-acetonitrile. Nine fractions eluted (500 µl each) was applied to 477A Sequencer (manufactured by Applied Biochemicals Co.) for analysis on serial sequencing of the amino acid sequence of the constituent peptide. As the result, the amino acid sequences of polypeptides in 8 fractions eluted were determined. The results of determining the amino acid sequence of each fragment are shown in SEQ ID NOS: 6 through 13. The oligopeptide, which structure was not determined, is considered to be located at the N terminus of 23 kilodaltons because of its blocked N terminus. The amino acid sequences of the constituent peptides, which structures were determined, could be all located on the amino acid sequence deduced in SEQ ID NO: 4. The results strongly suggest that the protein having a molecular weight of 23 kilodaltons would coincide with the protein encoded by the gene determined in Examples 6 and 7.

EXAMPLE 9

Determination of N-terminal Amino Acid Sequence of the Precursor Protein Obtained by Lysyl Endopeptidase Degradation In order to determine the lysyl endopeptidase fragment of 38 amino acid residues blocked at the N terminus as shown in Example 8, this constituent peptide was further fragmented by degradation with trypsin, and the amino acid sequence of 26 to 38 residues at the C terminus was determined. Next, the remaining N-terminal fragment was degraded by chymotrypsin to determine the amino acid sequence of the peptide from 8 to 25 residues at the C terminus. Subsequently the N-terminal peptide was degraded by an acylamino acid releasing enzyme to determine the sequence of 2 to 6 amino acid residues. As the result, all of the amino acid sequences among the blocked N-terminal lysyl endopeptidase fragments were determined, except for the acylated N-terminal amino acid residue and the seventh amino acid residue. The thus determined amino acid sequence is shown in SEQ ID NO: 5. The sequence indicated in SEQ ID NO: 5 deduced from the nucleotide sequence contains the N-terminal and seventh amino acid residues. As the result of analysis of the thus obtained amino acid sequence, the fragment described above was located in the region containing the oligopeptide sequence having a neurotrophic factor activity which was present in the N terminus of the amino acid sequence encoded by the precursor gene determined by the nucleotide sequencing determined in Examples 6 and 7.

In recent years, it is noted that most of the N termini of rat HCNP were acylated. According to the present invention, it has been revealed that the N terminus was already acylated at the stage of the precursor polypeptide.

As described in Example 3 in detail, the molecular weight of the precursor protein in which expression was noted in rat brain was assumed to be 23 kilodaltons based on the results of Western blotting but it was different from the molecular weight (21 kilodaltons) calculated from the amino acid sequence deduced from the nucleotide sequence of the gene determined. This difference in molecular weight was also noted in the case of bovine phosphatidylethanolamine binding protein (Reference 9) and it is assumed that mobility of the protein would be influenced in polyacrylamide gel electrophoresis due to steric structure of the protein, etc.

EXAMPLE 10

Screening of Human cDNA Gene Corresponding to the Precursor Gene Containing Rat HCNP In order to isolate human cDNA clone, human placenta brain cDNA library and human placenta cDNA library (both manufactured by Clontech Co.) were screened using rat HCNP precursor cDNA clone as a probe. The phage containing each of the human tissue-derived cDNA libraries described above was infected to E. coli Y1090 and $1\times10^6$ pfu of the phage was inoculated on 10 plates, respectively. The phage particles were transfered onto a nitrocellulose filter (manufactured by Scheicher And Schuell Co.). After treating twice in denaturation solution (0.1N NaOH, 1M NaCl) for 5 minutes and then twice in neutralization solution (3M NaCl, 1M Tris-HCl (pH 7.5)) for 5 minutes, the filter was dipped in 2×SSC solution (0.3M NaCl, 0.03M sodium citrate), dried and baked at 80° C. for 3 hours.

The EcoRI fragment of about 1 Kb contained in rat HCNP precursor cDNA clone (R4) (described in Example 6) was labeled with $^{32}P$ by Random Prime Labeling Kit (manufactured by Amersham Co.), heated and denatured at 95° C. for 10 minutes, which was then used as a probe. The nitrocellulose filter to which the phage had been immobilized was prehybridized at 37° C. for 4 hours in a solution containing 50% formamide, 5×SSC, 1% SDS, 0.2% Ficol, 0.2% polyvinylpyrrolidone and 0.2% bovine serum albumin. The filter was further shaken overnight in the same solution as described above containing the probe described above to effect hybridization.

The filter was washed in 2×SSC for 30 minutes at room temperature and then in 2×SSC and 1% SDS for further 2 hours at 50° C. After drying, the filter was applied to autoradiography. As the result, about 10 positive plaques per $1\times10^5$ pfu were obtained. By repeating 3 cycles of these procedures, each clone was isolated. Among these positive plaques, 15 clones (fb-1 to fb-15) and 4 clones (p1-1, 3, 4 and 5) were selected, respectively, from human fetal brain cDNA library and human placenta cDNA library, as those showing particularly strong signals. DNA prepared from these 19 in total phage clones according to the procedures shown in Example 6 was digested with EcoRI to examine the size of cDNA insert. The EcoRI fragment of the clone (p1-3) having the longest cDNA insert (1.4 kb) was subcloned to EcoRI site of pBluescript II vector (manufactured by Stratagene Co.).

EXAMPLE 11

Determination of Nucleotide Sequence of Human cDNA Gene Corresponding to the Precursor Gene Containing Rat HCNP The nucleotide sequence of cDNA subcloned to pBluescript II vector as shown in Example 10 described above was determined by the procedures of Example 6. The results indicate that p1-3 contained the open reading frame starting with ATG as initiation codon of eukaryote but did not contain either the sequence coincident with AATAAA sequence which is poly(A) additional signal or poly(A) sequence. The nucleotide sequence of cDNA containing the open reading frame is shown in SEQ ID NO: 14. The amino acid sequence deduced from the nucleotide sequence shown in SEQ ID NO: 14 is also shown in SEQ ID NO: 15. The amino acid sequence described does not contain methionine encoded by initiation codon ATG. The amino acid sequence which can be inferred is composed of 186 amino acids.

Among them, the oligopeptide shown in SEQ ID NO: 17 corresponds to the region from the first amino acid (proline) to the eleventh amino acid (leucine) of the polypeptide shown in SEQ ID NO: 15. The nucleotide sequence encoding human-derived neurotrophic peptide is also shown in SEQ ID NO: 16.

EXAMPLE 12

Synthesis of hHCNP(1-11) (SEQ ID NO: 17)

Chloromethylated polystyrene vinylbenzene resin (1% divinylbenzene with an initial chloride loading of 0.64 mmol/g of the resin) having a particle diameter of 100 to 200 mesh was employed. Upon synthesis of the polypeptide, 4.79 g of Boc-leu-OH was dissolved in a mixture of 45 ml of ethyl alcohol and 15 ml of water and pH was adjusted to 7 with 20% cesium carbonate solution. The solution was concentrated in vacuo and desicated. To the residue was added 220 ml of DMF and further added 20 g of the chloromethylated resin. The mixture was stirred at 50° C. for 24 hours to esterify. The resulting Boc-Leu-O-resin was filtered and washed sequentially with 90% DMF, DMF and ethyl alcohol and then desicated. Yield, 21.8 g.

Six grams of this Boc-Leu-O-resin were charged in a solid phase synthesis reactor. Following Schedule 1 described hereinafter, Boc-Pro-OH, Boc-Gly-OH, Boc-Ser(Bzl)-OH, Boc-Trp-OH, Boc-Lys(ClZ)-OH, Boc-Ser(Bzl)-OH, Boc-Leu-OH, Boc-Asp(OcHex)-OH, Boc-Val-OH and Boc-Pro-OH were successively coupled with the resin. As the result, 11.9 g of hHCNP(1-11) peptide resin was obtained.

To 6.00 g of this hHCNP(1-11) peptide resin were added 9 ml of anisole, 1.5 ml of ethylmethyl sulfide and 60 ml of anhydrous hydrogen fluoride. The mixture was reacted at −20° C. for 60 minutes and then at 0° C. for 60 minutes. After the reaction mixture was concentrated in vacuo, 200 ml of diethyl ether was added to the residue. The slurry was stirred for 30 minutes, filtered and washed with 100 ml of diethyl ether. To the residue was added 200 ml of 5% acetic acid aqueous solution. After stirring for 30 minutes, the resin was filtered and washed with 100 ml of 5% acetic acid aqueous solution. The filtrate was lyophilized to give a crude peptide, which was dissolved in 100 ml of 0.1% TFA aqueous solution. The solution was applied to reverse phase YMC-A363 (S-5) ODS column (30 φ×250 mm) previously equilibrated with 0.1% TFA aqueous solution. After the column was washed with 0.1% TFA aqueous solution, the peptide was eluted with gradient of 0 to 26% acetonitrile in 480 minutes at a flow rate of 6.0 ml/min. The eluent was monitored at A280 nm. The fractions containing the desired product were collected and lyophilized to give 471.1 mg of hHCNP(1-11).

The thus obtained hHCNP(1-11) was eluted at retention time of 31.0 minutes with linear density gradient of 10–50% aqueous acetonitrile containing 0.1% TFA through reverse phase YMC-AM303(S-5)-ODS column (4.6 φ×250 mm). The amino acid analysis of the peptide coincided with the calculated values.

Amino Acid Analysis

Hydrolysis: 4N Methanesulfonic acid, 2% tryptamine, at 110° C. for 24 hours

Analysis method: PICO-TAG (reverse phase-PTC amino acid) method

Result:
  Asx: 1.12 (1)
  Ser: 2.24 (2)

Gly: 1.19 (1)
Pro: 2.11 (2)
Val: 1.07 (1)
*Leu: 2.00 (2)
Trp: 0.97 (1)
Lys: 0.82 (1)

*Leu was used as a standard amino acid. The values in parentheses indicate calculated values.

Schedule 1

| Steps | Time (min.) × Treatment times |
|---|---|
| 1. Washing with methylene chloride, 60 ml | 2 × 3 |
| 2. Deprotection with 50% TFA, 5% ethanediol, 45% methylene chloride (V/V), 60 ml | 3 × 1<br>20 × 1 |
| 3. Washing with methylene chloride, 60 ml | 2 × 2 |
| 4. Washing with methanol, 60 ml | 2 × 2 |
| 5. Neutralization with 10% triethylamine, 90% methylene chloride (V/V), 60 ml | 1 × 1 |
| 6. Washing with methanol, 60 ml | 2 × 1 |
| 7. Neutralization with 10% triethylamine, 90% methylene chloride (V/V), 60 ml | 1 × 1 |
| 8. Washing with methanol, 60 ml | 2 × 2 |
| 9. Washing with methylene chloride, 60 ml | 2 × 3 |
| 10. Coupling by the use of various amino group-protected amino acids (6 mmols), additive (HOBt or HONp) 50% DMF-50% methylene chloride (W/W), 30 ml | 5 × 1 |
| Solution of DCC (6 mmols) in methylene chloride, 12 ml | 120 × 1 |
| 11. Washing with 50% DMF, 50% methylene chloride (V/V), 60 ml | 2 × 2 |
| 12. Washing with methanol, 60 ml | 2 × 1 |
| 13. Neutralization with 10% triethylamine, 90% methylene chloride (V/V), 60 ml | 1 × 1 |
| 14. Washing with methanol, 60 ml | 2 × 2 |
| 15. Washing with methylene chloride, 60 ml | 2 × 2 |
| 16. Acetylation with 25% acetic anhydride, 75% methylene chloride (V/V), 60 ml | 15 × 1 |
| 17. Washing with methylene chloride 60 ml | 2 × 2 |
| 18. Washing with methanol, 60 ml | 2 × 2 |

After the coupling reaction in the step 10, where a small amount of the resin was subjected to ninhydrin test to show positive blue indicative of incompleteness of the coupling reaction, the coupling reaction was repeated using an amino acid of the same protection type. In the case of coupling subsequent to twice occurrences, DMF or 1-methyl-2-pyrrolidinone was used instead of 50% DMF-50% methylene chloride (V/V) and the coupling reaction was carried out for a maximum of 12 hours.

EXAMPLE 13

Synthesis of hHCNP(2-7) (SEQ ID NO: 18)

Chloromethylated polystyrene vinylbenzene resin (1% divinylbenzene with an initial chloride loading of 0.66 mmol/g of the resin) having a particle diameter of 100 to 200 mesh was employed. Upon synthesis of the polypeptide, 9.64 g of Boc-Trp-OH was dissolved in a mixture of 100 ml of ethyl alcohol and 34 ml of water and pH was adjusted to 7 with 20% cesium carbonate solution. The solution was concentrated in vacuo and desicated. To the residue was added 240 ml of DMF and further added 40.16 g of the chloromethylated resin. The mixture was stirred at 50° C. for 14 hours and at room temperature for further 14 hours to esterify. The resulting Boc-Trp-O-resin was filtered and washed sequentially with 90% DMF, DMF and ethyl alcohol and then desicated. Yield, 46.8 g.

Six grams of this Boc-Trp-O-resin were charged in a solid phase synthesis reactor. Following Schedule 1 described hereinabove, Boc-Lys(ClZ)-OH, Boc-Ser(Bzl)-OH, Boc-Leu-OH, Boc-Asp(OcHex)-OH and Boc-Val-OH were successively coupled with the resin. As the result, 8.83 g of hHCNP(2-7) peptide resin was obtained.

To 8.83 g of this hHCNP(2-7) peptide resin were added 14 ml of anisole, 2.2 ml of ethylmethyl sulfide and 100 ml of anhydrous hydrogen fluoride. The mixture was reacted at −20° C. for 90 minutes and then at 0° C. for 70 minutes. After the reaction mixture was concentrated in vacuo, 100 ml of diethyl ether was added to the residue. The slurry was stirred for 30 minutes, filtered and washed with 300 ml of diethyl ether and 300 ml of chloroform. To the residue was added 100 ml of 1N acetic acid aqueous solution. After stirring for 30 minutes, the resin was filtered and washed with 40 ml of 1N acetic acid aqueous solution. The filtrate was lyophilized to give 2.38 g of a crude peptide.

The resulting crude peptide was dissolved in 250 ml of water. The solution was applied to reverse phase YMC-R355-15/30-ODS column (50 φ×500 mm) previously equilibrated with 0.1% TFA aqueous solution. After the column was washed with 0.1% TFA aqueous solution, the peptide was eluted with gradient of 0 to 15% acetonitrile in 180 minutes and further to 35% acetonitrile in 300 minutes at a flow rate of 15 ml/min. The eluent was monitored at A220 nm. The fractions containing the desired product were collected and lyophilized to give 2.054 g of hHCNP(2-7).

The thus obtained hHCNP(2-7) was eluted at retention time of 13.2 minutes with linear density gradient of 20–50% aqueous acetonitrile containing 0.1% TFA through reverse phase YMC-AM303(S-5)-ODS column (4.6 φ×250 mm). The amino acid analysis of the peptide coincided with the calculated values.

Amino Acid Analysis

Hydrolysis: 4N Methanesulfonic acid, 2% tryptamine, at 110° C. for 24 hours
Analysis method: PICO-TAG (reverse phase-PTC amino acid) method
Result:
Asx: 1.13 (1)
Ser: 1.05 (1)
Val: 1.07 (1)
*Leu: 1.00 (1)
Trp: 0.80 (1)
Lys: 0.94 (1)

*Leu was used as a standard amino acid. The values in parentheses indicate calculated values.

EXAMPLE 14

Synthesis of hHCNP(6-11) (SEQ ID NO: 20)

Six grams of this Boc-Leu-O-resin described in Example 12 was charged in a solid phase synthesis reactor. Following Schedule 1 described in Example 12, Boc-Pro-OH, Boc-Gly-OH, Boc-Ser(Bzl)-OH, Boc-Trp-OH and Boc-Lys(ClZ)

-OH were successively coupled with the resin. As the result, 9.46 g of hHCNP(6-11) peptide resin was obtained.

To 9.46 g of this hHCNP(6-11) peptide resin were added 15 ml of anisole, 2.4 ml of ethylmethyl sulfide and 100 ml of anhydrous hydrogen fluoride. The mixture was reacted at −20° C. for 60 minutes and then at 0° C. for 70 minutes. After the reaction mixture was concentrated in vacuo, 100 ml of diethyl ether was added to the residue. The slurry was stirred for 30 minutes, filtered and washed with 150 ml of diethyl ether and 150 ml of chloroform. To the residue was added 100 ml of 1N acetic acid aqueous solution. After stirring for 30 minutes, the resin was filtered and washed with 50 ml of 1N acetic acid aqueous solution. The filtrate was lyophilized to give 2.82 g of a crude peptide.

The resulting crude peptide was dissolved in 200 ml of water. The solution was applied to reverse phase YMC-R355-15/30-ODS column (50 φ×500 mm) previously equilibrated with 0.1% TFA aqueous solution. After the column was washed with 0.1% TFA aqueous solution, the peptide was eluted with gradient of 0 to 7% acetonitrile in 180 minutes and further to 15% acetonitrile in 300 minutes at a flow rate of 15 ml/min. The eluent was monitored at A220 nm. The fractions containing the desired product were collected and lyophilized to give 1.194 g of hHCNP(6-11).

The thus obtained hHCNP(6-11) was eluted at retention time of 14.0 minutes with linear density gradient of 20–35% aqueous acetonitrile containing 0.1% TFA through reverse phase YMC-AM303(S-5)-ODS column (4.6 φ×250 mm). The amino acid analysis of the peptide coincided with the calculated values.

Amino Acid Analysis

Hydrolysis: 4N Methanesulfonic acid, 2% tryptamine, at 110° C. for 24 hours
Analysis method: PICO-TAG (reverse phase-PTC amino acid) method
Result:
  Ser: 1.11 (1)
  Gly: 1.25 (1)
  Pro: 1.06 (1)
  *Leu: 1.00 (1)
  Trp: 0.76 (1)
  Lys: 0.97 (1)

*Leu was used as a standard amino acid. The values in parentheses indicate calculated values.

EXAMPLE 15

Synthesis of hHCNP(4-8)NH$_2$

MBHA resin (1% divinylbenzene with an initial amino group loading of 0.76 mmol/g of the resin) having a particle diameter of 100 to 200 mesh was employed. This resin, 3.95 g, was charged in a solid phase synthesis reactor. Following Schedule 1 described in Example 12, synthesis was initiated from Step 3 and Boc-Ser(Bzl)-OH, Boc-Trp-OH, Boc-Lys (ClZ)-OH, Boc-Ser(Bzl)-OH and Boc-Leu-OH were successively coupled with the resin. As the result, 6.36 g of hHCNP(4-8)NH$_2$ peptide resin was obtained.

To 6.36 g of this hHCNP(4-8)NH$_2$ peptide resin were added 10 ml of anisole, 1.6 ml of ethylmethyl sulfide and 80 ml of anhydrous hydrogen fluoride. The mixture was reacted at −20° C. for 60 minutes and then at 0° C. for 70 minutes. After the reaction mixture was concentrated in vacuo, 100 ml of diethyl ether was added to the residue. The slurry was stirred for 30 minutes, filtered and washed with 150 ml of diethyl ether and 150 ml of chloroform. To the residue was added 100 ml of 1N acetic acid aqueous solution. After stirring for 30 minutes, the resin was filtered and washed with 50 ml of 1N acetic acid aqueous solution. The filtrate was lyophilized to give 1.98 g of a crude peptide.

The resulting crude peptide was dissolved in 200 ml of water. The solution was applied to reverse phase YMC-R355-15/30-ODS column (50 φ×500 mm) previously equilibrated with 0.1% TFA aqueous solution. After the column was washed with 0.1% TFA aqueous solution, the peptide was eluted with gradient of 0 to 11% acetonitrile in 180 minutes and further to 30% acetonitrile in 360 minutes at a flow rate of 15 ml/min. The eluent was monitored at A220 nm. The fractions containing the desired product were collected and lyophilized to give 0.715 g of hHCNP(4-8)NH$_2$.

The thus obtained hHCNP(4-8)NH$_2$ was eluted at retention time of 18.8 minutes with linear density gradient of 10–25% aqueous acetonitrile containing 0.1% TFA through reverse phase YMC-AM303(S-5)-ODS column (4.6 φ×250 mm). The amino acid analysis of the peptide coincided with the calculated values.

Amino Acid Analysis

Hydrolysis: 4N Methanesulfonic acid, 2% tryptamine, at 110° C. for 24 hours
Analysis method: PICO-TAG (reverse phase-PTC amino acid) method
Result:
  Ser: 2.09 (2)
  *Leu: 1.00 (1)
  Trp: 0.52 (1)
  Lys: 1.05 (1)

*Leu was used as a standard amino acid. The values in parentheses indicate calculated values.

EXAMPLE 16

I) Construction of Recombinant Vector Expressed in E. coli

In order to express the protein encoded by the precursor gene containing the rat hippocampus-derived and human-derived neurotrophic peptides, cDNA gene was transduced to expression vector pKK233-2 (manufactured by Clontech Co.) containing powerful trc promoter derived from fused promoter of trp-lac (References 71, 72). This expression vector has ATG sequence which is translation initiation codon in unique restriction enzyme site NcoI (CCATGG) and also has ribosome binding site of prokaryote at the upstream. The expression vector also has T1T2 terminater which is a powerful transcription termination signal of prokaryote. Transduction of cDNA to this expression vector and construction of expression vector were performed by the procedures shown in FIG. 5. Firstly, clones AO10-12 and p1-3cDNA were digested with EcoRI and the termini were rendered blunt with E. coli DNA polymerase I Klenow fragment. The reaction was carried out by mixing 100 µl of 67 mM Tris-HCl (pH 7.4), 6.7 mM MgCl$_2$, 1 mM 2-mercaptoethanol, 1 mM each of dATP, dGTP, dCTP and dTTP, 0.5 µg of DNA and 0.25 units of DNA polymerase I Klenow fragment and incubating at 37° C. for 30 minutes. After phenol-chloroform treatment, the sample was purified and concentrated by ethanol precipitation.

The cDNA was transduced to expression vector pKK233-2 DNA in which SmaI site was newly inserted, after digestion with NcoI and treatment with Mung bean nuclease for rendering the termini blunt, previously. The expression vector was constructed as follows.

The reaction solution (50 μl) having a composition of 30 mM sodium acetate (pH 4.6), 50 mM NaCl, 1 mM zinc acetate, 5% glycerol and 5 units/μl of Mung bean nuclease and containing 1 μg of pKK233-2 DNA which had previously been digested with NcoI was kept at 37° C. for 30 minutes to render the termini blunt. Then, Sma I linker phosphorylated at the 5' end (manufactured by Toyobo Co.) was added thereto. Conditions for the linker addition reaction are as follows. After 100 μl of reaction solution (20 mM Tris-HCl (pH 7.6), 6.7 mM $MgCl_2$, 6.7 mM dithiothreitol, 1 mM ATP, 100 pmols of SmaI linker and 500 units of T4 DNA ligase) was incubated at 12° C. overnight, the reaction solution was heated at 65° C. for 10 minutes to inactivate the enzyme. Thereafter, expression vector treated as described above was transduced to E. coli JM109 to obtain transformants. The transformants bearing expression vector DNA newly added with SmaI site were selected. From the desired transformant, plasmid DNA was recovered. Digestion with SmaI was followed by treatment with E. coli alkaline phosphatase.

The rat hippocampus and human-derived precursor genes which were treated to render blunt were inserted into the expression vector treated as described above to construct recombinant vector. The recombinant vector was constructed under the following reaction conditions.

The reaction solution (10 μl) containing 20 mM Tris-HCl (pH 7.6), 6.7 mM $MgCl_2$, 6.7 mM dithiothreitol, 1 mM ATP, 0.1 μg of vector DNA, 0.5 μg of cDNA and 5 units of T4 DNA ligase was incubated at 12° C. overnight. Using 4 μl of the reaction solution, DNA was transduced to E. coli JM109 competent cells (manufactured by Toyobo Co.). The expression vector contains ampicillin resistant gene. Therefore, by plating competent cells on agar medium containing 50 μg of ampicillin, transformant were obtained. The clones appeared were inoculated one by one on a grid of a nitrocellulose membrane filter with grids. Incubation was performed overnight in agar medium added with ampicillin to form colony again. Plasmid DNA was fixed on the filter, as in the screening of the phage used in Example 7. Using R4cDNA as a probe, the desired clones (pKK233-2-AO1012, pKK233-2-p13) were obtained by colony hybridization (cf. FIG. 6).

II) Construction of Recombinant Vector Expressed in Mammal Culture Cell Line

In order to express the precursor protein containing rat hippocampus and human-derived neurotrophic peptide in mammal-derived culture cells, rat cDNA clone AO10-12 having nucleotide sequence obtained in Example 7 which is shown by SEQ ID NO: 3 and human cDNA clone p1-3 having nucleotide sequence shown by SEQ ID NO: 14 which was obtained in Example 11 were incorporated into expression vector to obtain E. coli transformant. The expression vector used was constructed as follows. The termini of 1.4 Kb HindIII fragment having LTR sequence derived from MMTV contained in pMDSG were treated by a modification of the process described in I) above to insert at the XbaI cleavage site of pBluescriptII (manufactured by Stratagene Co.). Then, BclI-EcoRI fragment (1 Kb) having poly(A) additional signal of SV40 T antigen was transduced to the aforesaid recombinant vector at the Xho cleavage site. Bam HI fragment (2.6 Kb) containing neomycin resistant genes of pMAM-neo (manufactured by Clontech Co.) was transduced to pVC19 previously inserted Kpn I linker into Sma I site at the Bam HI site. Then, neomycin resistant gene was cut out with Kpn I and transduced to the recombinant vector containing promoter and poly(A) additional sequence at the Kpn I site, which was made an expression vector (FIG. 6).

The EcoRI cDNA fragments of clones AO10-12 and p1-3 were introduced into the thus constructed expression vector at the EcoRI cleavage site and colony hybridization was performed in a manner similar to I) using R4cDNA as a probe to obtain the desired clones.

The thus obtained clones are named pMMTV-LTR-AO1012 and pMMTV-LTR-p13 (FIG. 6).

EXAMPLE 17

Preparation, Incubation and Expression of Transformants

I) Expression of Precursor Protein in E. coli

The recombinant vector-bearing transformants obtained were cultured in 3 ml of liquid medium supplemented with 2 mM isopropyl-β-D-thiogalactopyranoside (IPTG) to reach the late exponential growth phase. Transformed E. coli was collected by centrifugation. E. coli was suspended in 60 μl of SDS-containing sample buffer (50 mM Tris-HCl (pH 6.8), 100 mM dithiothreitol, 2% SDS, 0.1% Bromophenol Blue (BPB), 10% glycerol). The suspension was heated at 100° C. for 4 minutes to solubilize the protein. Using 20 μl corresponding to 1/3 of the sample, 12% polyacrylamide gel electrophoresis containing 1% SDS was performed (Reference 68). The proteins were then transferred to Immobilon PVDF Transfer Membrane manufactured by Millipore Co. (Reference 69) and the desired proteins produced by the transformants bearing rat and human cDNA genes were detected by a modification of the method for detection of the precursor protein described in Example 3 using the polyclonal antibody to rat HCNP (Reference 70). As the result, rat and human precursor proteins produced by the transformants were detected, confirming that the recombinant vector exhibits the function of expression as expected.

II) Expression of Precursor Protein in Mammal Culture Cells

30 μg of recombinant DNA prepared from the recombinant vector-bearing transformant of E. coli was transfected by DNA Transfection Kit (manufactured by Pharmacia Fine Chemicals, Inc.). The cells used were mouse fetal fibroblast-derived NIH/3T3 cells. $1 \times 10^6$ cells/dish of 10 cm in diameter were spread and the genes were transfected by DNA-calcium phosphate coprecipitation. The genes were transfected by a modification of the procedures instructed by Pharmacia Fine Chemicals. The transformant showing neomycin-resistant expression selectivity was obtained by continuing incubation in 10% bovine serum-containing DMEM medium supplemented with 400 μg/ml of neomycin (Genteticin: G418). The cells adhered to one plate was peeled off with 0.25% trypsin solution and again inoculated on 7 plates. Incubation was continued for further 2 weeks to obtain monoclones. Each monoclone was further cultured and chromosomal DNA was prepared from the neomycin-resistant cells.

The obtained chromosomal DNA was digested with EcoRI. The digestion product was isolated by 0.7% agarose gel electrophoresis and subjected to hybridization using R4cDNA as a probe (Reference 10). As the result, it was confirmed that transformed NIH/3T3 cells bearing the desired rat and human precursor proteins were obtained.

The thus obtained transformants were cultured in medium supplemented with 1 μM of glucocorticoid (dexamethasone) for 3 days to promote transcription from the promoter present in LTR sequence in MMTV. Then the cells were collected and examined if the precursor proteins were expressed. As described in I) above, the proteins in the transformants were solubilized and applied to polyacrylamide gel electrophoresis; the proteins were adsorbed to Immobilon PVDF filter by Western blotting and the desired proteins were detected by polyclonal antibody to rat HCNP.

As the result, the desired rat and human precursor proteins were detected from mammalian culture cell-derived transformants, indicating that the expression vector normally functions.

EXAMPLE 18

Assay for Biological Activity

The peptides were assayed for a biological activity in accordance with the method of Ojika et al. [Japanese Journal of Psycopharmacology, 7, 447–451 (1987)]. Namely, medial septum nucleous removed from rat embryonal brain (16 day embryo) is cut to small pieces, then the pieces were cultured in the Bottenstein's modified $N_2$ medium containing 1% FCS of saturation concentration, in Falcon's 35 mm plastic culture dish with 7% $CO_2$ mixed air, at 36° C. The neurotrophic peptide or its derivative was added to the cultures at initial day. In a control group, no peptide is added. The neurotrophic peptide may be added to the culture at 3 days after the initial day. After 6 days culture, an acetylcholine synthesis activity of cultured tissue was assayed to determine the biological activity of the peptide. The acetylcholine synthesis activity was assayed as follows.

A cultured tissue was pre-incubated in high potassium Tyrode solution buffered with Tris-HCl (pH 7.4) containing 98 mM of NaCl and 55 mM of KCl, then incubated in a buffered solution containing 100 nM [$^3$H] choline chloride (15 Ci/mmol) at 37° C. for 30 minutes. After washing out of free [$^3$H] choline, the tissue was dissolved in 1N formic acid/acetone (15:85) solution. Free [$^3$H] choline was converted to phosphocholine by choline kinase (0.1 unit/ml) and [$^3$H] acetylcholine was extracted with tetraphenyl boron (5 mg/ml acetonitrile) to determine the acetylcholine synthesis activity. The activity of cultured tissue for synthesis of acetylcholine was defined as an amount of synthesized acetylcholine per piece of cultured tissue.

Biological activity of hHCNP(1-11) obtained in Example 12 and hHCNP(6-11) obtained in Example 14 is shown in FIG. 7 and FIG. 8.

References:

1) Japanese Patent Application KOKAI (Laid-Open) No. 3-72499
2) EP-A-0390602
3) Angelettti and Bradshow: Proc. Natl. Acad. Sci. USA, 68, 2417, 1971
4) J. Leiblock et al.: Nature, 341, 149, 1989
5) F. Collins et al.: Science, 246, 1023, 1989
6) A. Hohn et al.: Nature, 344, 339, 1990
7) P. C. Maisonpierre et al.: Science, 247, 1446, 1990
8) Y. Kaisho et al.: FEBS Letters, 266, 187, 1990
9) F. Schoentgen et al.: Eur. J. Biochem., 166, 333, 1987
10) J. Sambrook et al.: "Molecular Cloning—A laboratory manual, 2nd. ed.", Cold Spring Harbor Lab., New York, 1989
11) J. Favaloro et al.: Methods in Enzymol., 65, 718, 1980
12) V. Glisin et al.: biochem., 13, 2633, 1974
13) A. Ullrich et al.: Science, 196, 1313, 1977
14) M. Edmonds et al.: Proc. Natl. Acad. Sci. USA, 68, 1336, 1971
15) H. Aviv and P. Leder: Proc. Natl. Acad. Sci. USA, 69, 1408, 1972
16) R. F. Schleif and P. C. Wensink: "Practical Methods in Molecular Biology", Springer-Verlag, New York, 1981
17) J. B. Gurdon et al.: Nature, 233, 177, 1972
18) J. B. Gurdon: "The control of gene expression in animal development", Oxford University Press, 1974
19) U. Gubler and B. J. Hoffman: Gene, 25, 263, 1983
20) C. Schneider et al.: Nature, 311, 675, 1984
21) H. Haymerle et al.: Nucl. Acid. Res., 14, 8615, 1986
22) S. Koike et al.: Nucl. Acid. Res., 15, 2499, 1987
23) T. V. Huynh et al.: "DNA Cloning—A practical approach", IRL press, Oxford, 1985
24) G. Schere et al.: Devel. Biol., 86, 438, 1981
25) R. A. Young and R. W. Davis: Science, 222, 778, 1983
26) R. A. Young and R. W. Davis: Proc. Natl. Acad. Sci. USA, 80, 1194, 1983
27) K. Itakura et al.: Science, 198, 1056, 1977
28) J. H. Miller and W. S. Peznikoff: "The Operon", Cold Spring Harbor Lab., New York, 1978
29) D. W. Mount: Ann. Rev. Genet., 14, 279, 1980
30) A. Efstratiadis and L. Villa-Komaroff: "In Genetic Engineering", Plenum press, New York, 1979
31) C. Chen and H. Okayama: Mol. Cell. Biol., 7, 2745, 1987
32) D. Hanahan: J. Mol. Biol., 166, 557, 1983
33) D. Hanahan: "DNA Cloning—A practical approach", IRL press, Oxford, 1985
34) J. L. Guesden et al.: J. Histochem. Cytochem., 27, 1131, 1979
35) C. Bonnard et al.: "Immunolabelling for electron microscopy", Elseiver Scientific Publishers, Amsterdam, 1984
36) J. J. Leary et al.: Proc. Natl. Acad. Sci., USA, 80, 4045, 1983
37) D. M. Helfman et al.: Proc. Natl. Acad. Sci. USA, 80, 31, 1983
38) M. S. Blake et al.: Anal. Biochem., 136, 176, 1984
39) F. Boliver et al.: Gene, 2, 95, 1977
40) D. V. Goeddel et al.: Nature, 281, 544, 1979
41) D. V. Goeddel et al.: Nucl. Acid. Res., 8, 4057, 1980
42) D. V. Goeddel et al.: Proc. Natl. Acad. Sci. USA, 76, 106, 1979
43) D. V. Goeddel et al.: Nature, 287, 411, 1980
44) J. Yochem and B. Byers: J. Mol. Biol., 195, 233, 1987
45) M. Karin et al.: Proc. Natl. Acad. Sci. USA, 81, 337, 1984
46) R. A. Hitzeman et al.: J. Biol. Chem., 255, 2073, 1980
47) V. M. Williamson et al.: Mol. Cell. Biol., 3, 20, 1983
48) M. J. Holland et al.: J. Biol. Chem., 256, 1385, 1981
49) N. J. Ptoudfoot and C. G. Brownlee: Nature, 263, 211, 1976
50) R. G. Hawley et al.: Proc. Natl. Acad. Sci. USA, 84, 2406, 1987
51) G. Brady et al.: The EMBO J., 4, 2583, 1985
52) F. Lee et al.: Nature, 294, 228, 1981
53) G. Ringold et al.: J. Mol. Applied Genet., 1, 165, 1981
54) M. Wigler et al.: Cell, 14, 725, 1978
55) C. M. Corsano and M. L. Pearson: Somat. Cell Genet. 7, 603, 1981
56) F. L. Graham and A. J. van der Eb: Virology, 52, 456, 1973
57) M. Rassoulzadegon: Nature, 295, 257, 1982
58) H. Potter et al.: Proc. Natl. Acad. Sci. USA, 81, 7161, 1984
59) G. Chu et al.: Nucl. Acid. Res. 15, 1311, 1987
60) K. Thomas: "Transgenic Animals", Butterworth-Heinemann Co., 1991, chapter 4, p. 45–54
61) M. Bodansky and M. A. Ondetti: "Peptide Synthesis", Interscience, New York, 1966

62) F. M. Finn and K. Hofmann: "The Proteins", vol. 2 Academic Press Inc., New York, 1976
63) N. Izumiya et al.: "PEPTIDE SYNTHESIS", Maruzen Co., Ltd., 1975
64) N. Izumiya et al.: "BASIS AND EXPERIMENT OF PEPTIDE SYNTHESIS", Maruzen Co., Ltd., 1985
65) H. Yajima: "Lecture Series on Biochemical Experiment: Chemistry of Protein IV", edited by Japanese Biochemical Association, 1977
66) K. Ojika et al.: Jpn. J. Psychopharmacol., 447–451 (1987)
67) K. Ogawa et al.: "TECHNOLOGY OF HISTOCYTOLOGY: HORMONE AND NEUROTRANSMITTANT SUBSTANCE", Asakura Shoten Publishing Co., 1986
68) U. K. Laemmli: Nature, 227, 680, 1970
69) T. Manabe et al.: Anal. Biochem., 143, 39, 1984
70) I. Sakurabayashi et al: "GENE, PROTEIN: EXPERIMENTAL MANUAL, BLOTTING", Soft Science Co., 1987
71) E. Amann and J. Broslus: Gene, 40, 183, 1985
72) D. Straus and W. Gilbert: Proc. Natl. Acad. Sci. USA, 82, 2914, 1985

We claim:

1. A purified neurotropic peptide having neurotropic activity consisting of an amino acid sequence selected from the group consisting of amino acids 1–11 of SEQ ID NO: 17, amino acids 2–11 of SEQ ID NO: 17, amino acids 3–11 of SEQ ID NO: 17, amino acids 4–11 of SEQ ID NO: 17, amino acids 5–11 of SEQ ID NO: 17, and amino acids 6–11 of SEQ ID NO: 17.

2. The purified neurotropic peptide of claim 1, wherein the N-terminus of said peptide is bound to a substituent represented by the following formula 1:

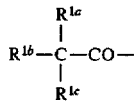

wherein $R^{1a}$ represents H, an unsubstituted or substituted alkyl, hydroxy, —COOH, an aryl, a $C_1$–$C_4$ alkoxy, a halogen atom, —CONR$_2$R$_3$ wherein each of $R^2$ and $R^3$ independently represents H or a $C_1$–$C_4$ alkyl, or a heterocyclic group; wherein $R^{1b}$ represents H, an unsubstituted or substituted alkyl or a halogen atom; and wherein $R^{1c}$ represents H, a $C_1$–$C_4$ alkyl or a halogen atom; and/or the C-terminus of said peptide is bound to a substituent represented by the following formula 3:

wherein $R^{8a}$ represents H, an unsubstituted or substituted alkyl, hydroxy, an aryl or a heterocyclic group; and wherein $R^{8b}$ represents H or an unsubstituted or substituted alkyl.

3. A purified neurotropic peptide having neurotropic activity represented by the amino acid sequence of SEQ ID NO: 17.

4. A pharmaceutical composition comprising, as an active ingredient, a purified neurotrophic peptide according to any one of claims 1–3, and a pharmaceutically acceptable carrier.

5. A purified precursor polypeptide of a neurotrophic peptide represented by the amino acid sequence as depicted in SEQ ID NO: 15.

* * * * *

SEQUENCE LISTING ( 1 ) GENERAL INFORMATION:

( i i i ) NUMBER OF SEQUENCES: 25

( 2 ) INFORMATION FOR SEQ ID NO:1:

( i ) SEQUENCE CHARACTERISTICS:
        ( A ) LENGTH: 33 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
        ( A ) ORGANISM: Rattus norvegicus
        ( B ) STRAIN: Wistar
        ( F ) TISSUE TYPE: hippocampal tissue of brain ( v i i ) IMMEDIATE SOURCE:
        ( B ) CLONE: A010-12

( i x ) FEATURE:
        ( A ) NAME/KEY: CDS
        ( B ) LOCATION: 1..33

( x i ) SEQUENCE DESCRIPTION: SEQ ID NO:1:

```
GCC  GCC  GAC  ATC  AGC  CAG  TGG  GCC  GGG  CCG  CTG                      33
Ala  Ala  Asp  Ile  Ser  Gln  Trp  Ala  Gly  Pro  Leu
 1                 5                           1 0
```

( 2 ) INFORMATION FOR SEQ ID NO:2:

( i ) SEQUENCE CHARACTERISTICS:
        ( A ) LENGTH: 11 amino acids
        ( B ) TYPE: amino acid
        ( D ) TOPOLOGY: linear ( i i ) MOLECULE TYPE: protein ( v i ) ORIGINAL SOURCE:
        ( A ) ORGANISM: rattus norvegicus
        ( B ) STRAIN: Wistar
        ( F ) TISSUE TYPE: hippocampal tissue of brain ( i x ) FEATURE:
        ( A ) NAME/KEY: Peptide
        ( B ) LOCATION: 1..11

( x i ) SEQUENCE DESCRIPTION: SEQ ID NO:2:

```
Ala  Ala  Asp  Ile  Ser  Gln  Trp  Ala  Gly  Pro  Leu
 1                 5                           1 0
```

( 2 ) INFORMATION FOR SEQ ID NO:3:

( i ) SEQUENCE CHARACTERISTICS:
        ( A ) LENGTH: 1047 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
        ( A ) ORGANISM: Rattus norvegicus
        ( B ) STRAIN: Wistar
        ( F ) TISSUE TYPE: hippocampal tissue of brain ( v i i ) IMMEDIATE SOURCE:
        ( B ) CLONE: A010-12

( i x ) FEATURE:
        ( A ) NAME/KEY: CDS
        ( B ) LOCATION: 26..586

( i x ) FEATURE:
        ( A ) NAME/KEY: 5'UTR
        ( B ) LOCATION: 1..25

( i x ) FEATURE:
        ( A ) NAME/KEY: mat_peptide
        ( B ) LOCATION: 26..586

( i x ) FEATURE:
        ( A ) NAME/KEY: 3'UTR
        ( B ) LOCATION: 587..1047

( i x ) FEATURE:
        ( A ) NAME/KEY: polyA_site
        ( B ) LOCATION: 1008..1047

( i x ) FEATURE:
        ( A ) NAME/KEY: polyA_signal
        ( B ) LOCATION: 987..992

( x i ) SEQUENCE DESCRIPTION: SEQ ID NO:3:

```
GCGTGTGTCT GTTCTCTCCA TCGTC ATG GCC GCC GAC ATC AGC CAG TGG GCC         52
                            Met Ala Ala Asp Ile Ser Gln Trp Ala
                             1               5

GGG CCG CTG TCA CTA CAG GAG GTG GAT GAG CCG CCC CAG CAC GCC CTG        100
Gly Pro Leu Ser Leu Gln Glu Val Asp Glu Pro Pro Gln His Ala Leu
 10              15                  20                  25

AGG GTC GAC TAC GGC GGA GTA ACG GTG GAC GAG CTG GGC AAA GTG CTG        148
Arg Val Asp Tyr Gly Gly Val Thr Val Asp Glu Leu Gly Lys Val Leu
                 30                  35                  40

ACG CCC ACC CAG GTC ATG AAT AGA CCA AGC AGC ATT TCA TGG GAT GGC        196
Thr Pro Thr Gln Val Met Asn Arg Pro Ser Ser Ile Ser Trp Asp Gly
             45                  50                  55

CTT GAT CCT GGG AAG CTC TAC ACC CTG GTC CTC ACA GAC CCC GAT GCT        244
Leu Asp Pro Gly Lys Leu Tyr Thr Leu Val Leu Thr Asp Pro Asp Ala
         60                  65                  70

CCC AGC AGG AAG GAC CCC AAA TTC AGG GAG TGG CAC CAC TTC CTG GTG        292
Pro Ser Arg Lys Asp Pro Lys Phe Arg Glu Trp His His Phe Leu Val
     75                  80                  85

GTC AAC ATG AAG GGC AAC GAC ATT AGC AGT GGC ACT GTC CTC TCC GAA        340
Val Asn Met Lys Gly Asn Asp Ile Ser Ser Gly Thr Val Leu Ser Glu
 90                  95                 100                 105

TAC GTG GGC TCC GGA CCT AAA GAC ACA GGT CTG CAC CGC CGC TAC GTC        388
Tyr Val Gly Ser Gly Pro Lys Asp Thr Gly Leu His Arg Arg Tyr Val
                110                 115                 120
```

| | | | | | | | | | | | | | | | | |
|---|---|---|---|---|---|---|---|---|---|---|---|---|---|---|---|---|
|TGG|CTG|GTG|TAT|GAG|CAG|GAG|CAG|CCT|CTG|AAC|TGT|GAC|GAG|CCC|ATC|436|
|Trp|Leu|Val|Tyr|Glu|Gln|Glu|Gln|Pro|Leu|Asn|Cys|Asp|Glu|Pro|Ile| |
| | |125| | | | |130| | | | |135| | | | |

```
CTC  AGC  AAC  AAG  TCT  GGA  GAC  AAC  CGC  GGC  AAG  TTC  AAG  GTG  GAG  TCC        484
Leu  Ser  Asn  Lys  Ser  Gly  Asp  Asn  Arg  Gly  Lys  Phe  Lys  Val  Glu  Ser
          140                      145                      150

TTC  CGC  AAG  AAG  TAC  CAC  CTG  GGA  GCC  CCG  GTG  GCC  GGC  ACG  TGC  TTC        532
Phe  Arg  Lys  Lys  Tyr  His  Leu  Gly  Ala  Pro  Val  Ala  Gly  Thr  Cys  Phe
          155                      160                      165

CAG  GCA  GAG  TGG  GAT  GAC  TCT  GTG  CCC  AAG  CTG  CAT  GAT  CAG  TCG  GCT        580
Gln  Ala  Glu  Trp  Asp  Asp  Ser  Val  Pro  Lys  Leu  His  Asp  Gln  Ser  Ala
170                      175                      180                      185

GGG  AAG  TAGGGCGCT  GCAGAGCCCG  CAGCCCCGGG  GACCCCACAG  TACAGTCAAG                   636
Gly  Lys

TCGTATAAAG  CATGTCTGTG  GGGTGTCCCC  CCACGCCCAT  CCTTCCTTCC  CACCCTCTCA                696

TAGGGAGTTC  TCAGTTGTGC  TAGGTACAG   CTCTAGGATG  TCTTCCACTT  TGTCCAGGAC                756

CAGGCCCAGT  AACATCTTTT  GGGGTGGGCT  TATCAATCCT  CCCATCTCGG  CTGAGCCCTG                816

ACCGCCCAGG  TCAGATGGCT  GCATAGTTAT  CAATATTCCT  GGGCTGCTGC  TACGCAGTGC                876

TGCTGTGTGG  AGGCCAGGCT  GTGGAGAGAG  ACCCTGTTAG  CCCCTTACAT  CCCAGTGGGA                936

TAAGCAAAAG  TCACCGGAGT  TGCTGGGCGT  GTTAAACCTC  ATCAAATACA  AATAAAGGGC                996

ATTGCATTCA  GAAAAAAAAA  AAAAAAAAAA  AAAAAAAAAA  AAAAAAAAA  A                         1047
```

(2) INFORMATION FOR SEQ ID NO:4:

(i) SEQUENCE CHARACTERISTICS:
        (A) LENGTH: 187 amino acids
        (B) TYPE: amino acid
        (D) TOPOLOGY: linear (ii) MOLECULE TYPE: protein (xi) SEQUENCE DESCRIPTION: SEQ ID NO:4:

```
Met  Ala  Ala  Asp  Ile  Ser  Gln  Trp  Ala  Gly  Pro  Leu  Ser  Leu  Gln  Glu
 1                    5                    10                        15

Val  Asp  Glu  Pro  Pro  Gln  His  Ala  Leu  Arg  Val  Asp  Tyr  Gly  Gly  Val
               20                       25                        30

Thr  Val  Asp  Glu  Leu  Gly  Lys  Val  Leu  Thr  Pro  Thr  Gln  Val  Met  Asn
          35                        40                   45

Arg  Pro  Ser  Ser  Ile  Ser  Trp  Asp  Gly  Leu  Asp  Pro  Gly  Lys  Leu  Tyr
     50                        55                   60

Thr  Leu  Val  Leu  Thr  Asp  Pro  Asp  Ala  Pro  Ser  Arg  Lys  Asp  Pro  Lys
 65                  70                   75                        80

Phe  Arg  Glu  Trp  His  His  Phe  Leu  Val  Val  Asn  Met  Lys  Gly  Asn  Asp
               85                        90                        95

Ile  Ser  Ser  Gly  Thr  Val  Leu  Ser  Glu  Tyr  Val  Gly  Ser  Gly  Pro  Lys
               100                      105                      110

Asp  Thr  Gly  Leu  His  Arg  Arg  Tyr  Val  Trp  Leu  Val  Tyr  Glu  Gln  Glu
               115                      120                      125

Gln  Pro  Leu  Asn  Cys  Asp  Glu  Pro  Ile  Leu  Ser  Asn  Lys  Ser  Gly  Asp
     130                      135                      140

Asn  Arg  Gly  Lys  Phe  Lys  Val  Glu  Ser  Phe  Arg  Lys  Lys  Tyr  His  Leu
145                      150                      155                      160

Gly  Ala  Pro  Val  Ala  Gly  Thr  Cys  Phe  Gln  Ala  Glu  Trp  Asp  Asp  Ser
               165                      170                      175

Val  Pro  Lys  Leu  His  Asp  Gln  Ser  Ala  Gly  Lys
               180                      185
```

( 2 ) INFORMATION FOR SEQ ID NO:5:

( i ) SEQUENCE CHARACTERISTICS:
        ( A ) LENGTH: 38 amino acids
        ( B ) TYPE: amino acid
        ( C ) STRANDEDNESS: single
        ( D ) TOPOLOGY: linear ( i i ) MOLECULE TYPE: peptide ( v ) FRAGMENT TYPE: N-terminal ( v i ) ORIGINAL SOURCE:
        ( A ) ORGANISM: Rattus norvegicus
        ( B ) STRAIN: Wistar
        ( F ) TISSUE TYPE: hippocampal tissue of brain ( i x ) FEATURE:
        ( A ) NAME/KEY: Peptide
        ( B ) LOCATION: 1..38

( x i ) SEQUENCE DESCRIPTION: SEQ ID NO:5:

```
Ala Ala Asp Ile Ser Gln Trp Ala Gly Pro Leu Ser Leu Gln Glu Val
 1               5                  10                  15
Asp Glu Pro Pro Gln His Ala Leu Arg Val Asp Tyr Gly Gly Val Thr
            20                  25                  30
Val Asp Glu Leu Gly Lys
            35
```

( 2 ) INFORMATION FOR SEQ ID NO:6:

( i ) SEQUENCE CHARACTERISTICS:
        ( A ) LENGTH: 23 amino acids
        ( B ) TYPE: amino acid
        ( D ) TOPOLOGY: linear ( i i ) MOLECULE TYPE: peptide ( v ) FRAGMENT TYPE: internal ( v i ) ORIGINAL SOURCE:
        ( A ) ORGANISM: Rattus norvegicus
        ( B ) STRAIN: Wistar
        ( F ) TISSUE TYPE: hippocampal tissue of brain ( i x ) FEATURE:
        ( A ) NAME/KEY: Peptide
        ( B ) LOCATION: 1..23

( x i ) SEQUENCE DESCRIPTION: SEQ ID NO:6:

```
Val Leu Thr Pro Thr Gln Val Met Asn Arg Pro Ser Ser Ile Ser Trp
 1               5                  10                  15
Asp Gly Leu Asp Pro Gly Lys
            20
```

( 2 ) INFORMATION FOR SEQ ID NO:7:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( v ) FRAGMENT TYPE: internal ( v i ) ORIGINAL SOURCE:
        ( A ) ORGANISM: rattus norvegicus
        ( B ) STRAIN: Wistar
        ( F ) TISSUE TYPE: hippocampal tissue of brain ( i x ) FEATURE:
   ( A ) NAME/KEY: Peptide
   ( B ) LOCATION: 1..15

( x i ) SEQUENCE DESCRIPTION: SEQ ID NO:7:

Leu Tyr Thr Leu Val Leu Thr Asp Pro Asp Ala Pro Ser Arg Lys
1               5                   10                  15

( 2 ) INFORMATION FOR SEQ ID NO:8:

( i ) SEQUENCE CHARACTERISTICS:
      ( A ) LENGTH: 13 amino acids
      ( B ) TYPE: amino acid
      ( D ) TOPOLOGY: linear ( i i ) MOLECULE TYPE: peptide ( v ) FRAGMENT TYPE: internal ( v i ) ORIGINAL SOURCE:
      ( A ) ORGANISM: rattus norvegicus
      ( B ) STRAIN: Wistar
      ( F ) TISSUE TYPE: hippocampal tissue of brain ( i x ) FEATURE:
      ( A ) NAME/KEY: Peptide
      ( B ) LOCATION: 1..13

( x i ) SEQUENCE DESCRIPTION: SEQ ID NO:8:

Phe Arg Glu Trp His His Phe Leu Val Val Asn Met Lys
1               5                   10

( 2 ) INFORMATION FOR SEQ ID NO:9:

( i ) SEQUENCE CHARACTERISTICS:
      ( A ) LENGTH: 20 amino acids
      ( B ) TYPE: amino acid
      ( D ) TOPOLOGY: linear ( i i ) MOLECULE TYPE: peptide ( v ) FRAGMENT TYPE: internal ( v i ) ORIGINAL SOURCE:
      ( A ) ORGANISM: rattus norvegicus
      ( B ) STRAIN: Wistar
      ( F ) TISSUE TYPE: hippocampal tissue of brain ( i x ) FEATURE:
      ( A ) NAME/KEY: Peptide
      ( B ) LOCATION: 1..20

( x i ) SEQUENCE DESCRIPTION: SEQ ID NO:9:

Gly Asn Asp Ile Ser Ser Gly Thr Val Leu Ser Glu Tyr Val Gly Ser
1               5                   10                  15

Gly Pro Pro Lys
            20

( 2 ) INFORMATION FOR SEQ ID NO:10:

( i ) SEQUENCE CHARACTERISTICS:
      ( A ) LENGTH: 28 amino acids
      ( B ) TYPE: amino acid
      ( D ) TOPOLOGY: linear ( i i ) MOLECULE TYPE: peptide ( v ) FRAGMENT TYPE: internal ( v i ) ORIGINAL SOURCE:
      ( A ) ORGANISM: rattus norvegicus
      ( B ) STRAIN: Wistar
      ( F ) TISSUE TYPE: hippocampal tissue of brain (ix) FEATURE:
  (A) NAME/KEY: Peptide
  (B) LOCATION: 1..28

(xi) SEQUENCE DESCRIPTION: SEQ ID NO:10:

Asp Thr Gly Leu His Arg Tyr Val Trp Leu Val Tyr Glu Gln Glu Gln
1               5                   10                  15
Pro Leu Asn Cys Asp Glu Pro Ile Leu Ser Asn Lys
            20                  25

(2) INFORMATION FOR SEQ ID NO:11:

(i) SEQUENCE CHARACTERISTICS:
    (A) LENGTH: 6 amino acids
    (B) TYPE: amino acid
    (D) TOPOLOGY: linear (ii) MOLECULE TYPE: peptide (v) FRAGMENT TYPE: internal (vi) ORIGINAL SOURCE:
    (A) ORGANISM: rattus norvegicus
    (B) STRAIN: Wistar
    (F) TISSUE TYPE: hippocampal tissue of brain (ix) FEATURE:
    (A) NAME/KEY: Peptide
    (B) LOCATION: 1..6

(xi) SEQUENCE DESCRIPTION: SEQ ID NO:11:

Val Glu Ser Phe Arg Lys
1               5

(2) INFORMATION FOR SEQ ID NO:12:

(i) SEQUENCE CHARACTERISTICS:
    (A) LENGTH: 22 amino acids
    (B) TYPE: amino acid
    (D) TOPOLOGY: linear (ii) MOLECULE TYPE: peptide (v) FRAGMENT TYPE: internal (vi) ORIGINAL SOURCE:
    (A) ORGANISM: rattus norvegicus
    (B) STRAIN: Wistar
    (F) TISSUE TYPE: hippocampal tissue of brain (ix) FEATURE:
    (A) NAME/KEY: Peptide
    (B) LOCATION: 1..22

(xi) SEQUENCE DESCRIPTION: SEQ ID NO:12:

Tyr His Leu Gly Ala Pro Val Ala Gly Thr Cys Phe Gln Ala Glu Trp
1               5                   10                  15
Asp Asp Ser Val Pro Lys
            20

(2) INFORMATION FOR SEQ ID NO:13:

(i) SEQUENCE CHARACTERISTICS:
    (A) LENGTH: 8 amino acids
    (B) TYPE: amino acid
    (D) TOPOLOGY: linear (ii) MOLECULE TYPE: peptide (v) FRAGMENT TYPE: internal (v i) ORIGINAL SOURCE:
 (A) ORGANISM: rattus norvegicus
 (B) STRAIN: Wistar
 (D) DEVELOPMENTAL STAGE: hippocampal tissue of brain (i x) FEATURE:
 (A) NAME/KEY: Peptide
 (B) LOCATION: 1..8

(x i) SEQUENCE DESCRIPTION: SEQ ID NO:13:

```
Leu His Asp Gln Leu Ala Gly Lys
1               5
```

(2) INFORMATION FOR SEQ ID NO:14:

(i) SEQUENCE CHARACTERISTICS:
 (A) LENGTH: 1447 base pairs
 (B) TYPE: nucleic acid
 (C) STRANDEDNESS: double
 (D) TOPOLOGY: linear (i i) MOLECULE TYPE: cDNA to mRNA (i i i) HYPOTHETICAL: NO (i v) ANTI-SENSE: NO (v i) ORIGINAL SOURCE:
 (A) ORGANISM: Homo sapiens
 (F) TISSUE TYPE: placental tissue (v i i) IMMEDIATE SOURCE:
 (B) CLONE: p1-3

(i x) FEATURE:
 (A) NAME/KEY: CDS
 (B) LOCATION: 120..680

(i x) FEATURE:
 (A) NAME/KEY: 5'UTR
 (B) LOCATION: 1..119

(i x) FEATURE:
 (A) NAME/KEY: mat_peptide
 (B) LOCATION: 120..680

(i x) FEATURE:
 (A) NAME/KEY: 3'UTR
 (B) LOCATION: 681..1447

(x i) SEQUENCE DESCRIPTION: SEQ ID NO:14:

```
GAATTCGGGG GGGGGTCTGC GTCTTCCCGA GCCAGTGTGC TGAGCTCTCC GCGTCGCCTC      60

TGTCGCCCGC GCCTGGCCTA CCGCGGCACT CCCGGCTGCA CGCTCTGCTT GGCCTCGCC      119

ATG CCG GTG GAC CTC AGC AAG TGG TCC GGG CCC TTG AGC CTG CAA GAA       167
Met Pro Val Asp Leu Ser Lys Trp Ser Gly Pro Leu Ser Leu Gln Glu
 1               5                  10                  15

GTG GAC GAG CAG CCG CAG CAC CCG CTG CAT GTC ACC TAC GCC GGG GCG       215
Val Asp Glu Gln Pro Gln His Pro Leu His Val Thr Tyr Ala Gly Ala
             20                  25                  30

GCG GTG GAC GAG CTG GGC AAA GTG CTG ACG CCC ACC CAG GTT AAG AAT       263
Ala Val Asp Glu Leu Gly Lys Val Leu Thr Pro Thr Gln Val Lys Asn
         35                  40                  45

AGA CCC ACC AGC ATT TCG TGG GAT GGT CTT GAT TCA GGG AAG CTC TAC       311
Arg Pro Thr Ser Ile Ser Trp Asp Gly Leu Asp Ser Gly Lys Leu Tyr
     50                  55                  60

ACC TTG GTC CTG ACA GAC CCG GAT GCT CCC AGC AGG AAG GAT CCC AAA       359
Thr Leu Val Leu Thr Asp Pro Asp Ala Pro Ser Arg Lys Asp Pro Lys
 65                  70                  75                  80

TAC AGA GAA TGG CAT CAT TTC CTG GTG GTC AAC ATG AAG GGC AAT GAC       407
Tyr Arg Glu Trp His His Phe Leu Val Val Asn Met Lys Gly Asn Asp
```

|  |  |  |  |  |  |  |  |  |  |  |  |  |  |  |  |
|---|---|---|---|---|---|---|---|---|---|---|---|---|---|---|---|
|  |  |  | 85 |  |  |  |  | 90 |  |  |  |  | 95 |  |  |
| ATC | AGC | AGT | GGC | ACA | GTC | CTC | TCC | GAT | TAT | GTG | GGC | TCG | GGG | CCT | CCC | 455
| Ile | Ser | Ser | Gly | Thr | Val | Leu | Ser | Asp | Tyr | Val | Gly | Ser | Gly | Pro | Pro |
|  |  |  | 100 |  |  |  |  | 105 |  |  |  |  | 110 |  |  |

```
ATC AGC AGT GGC ACA GTC CTC TCC GAT TAT GTG GGC TCG GGG CCT CCC    455
Ile Ser Ser Gly Thr Val Leu Ser Asp Tyr Val Gly Ser Gly Pro Pro
            100                 105                 110

AAG GGC ACA GGC CTC CAC CGC TAT GTC TGG CTG GTT TAC GAG CAG GAC    503
Lys Gly Thr Gly Leu His Arg Tyr Val Trp Leu Val Tyr Glu Gln Asp
            115                 120                 125

AGG CCG CTA AAG TGT GAC GAG CCC ATC CTC AGC AAC CGA TCT GGA GAC    551
Arg Pro Leu Lys Cys Asp Glu Pro Ile Leu Ser Asn Arg Ser Gly Asp
    130                 135                 140

CAC CGT GGC AAA TTC AAG GTG GCG TCC TTC CGT AAA AAG TAT GAG CTC    599
His Arg Gly Lys Phe Lys Val Ala Ser Phe Arg Lys Lys Tyr Glu Leu
145                 150                 155                 160

AGG GCC CCG GTG GCT GGC ACG TGT TAC CAG GCC GAG TGG GAT GAC TAT    647
Arg Ala Pro Val Ala Gly Thr Cys Tyr Gln Ala Glu Trp Asp Asp Tyr
                165                 170                 175

GTG CCC AAA CTG TAC GAG CAG CTG TCT GGG AAG TAGGGGGTTA GCTTGGGGAC   700
Val Pro Lys Leu Tyr Glu Gln Leu Ser Gly Lys
                180                 185

CTGAACTGTC CTGGAGGCCC CAAGCCATGT TCCCCAGTTC AGTGTTGCAT GTATAATAGA    760
TTTCTCCTCT TCCTGCCCCC CTTGGCATGG GTGAGACCTG ACCAGTCAGA TGGTAGTTGA    820
GGGTGACTTT TCCTGCTGCC TGGCCTTTAT AATTTTACTC ACTCACTCTG ATTTATGTTT    880
TGATCAAATT TGAACTTCAT TTGGGGGGT ATTTTGGTAC TGTGATGGGG TCATCAAATT    940
ATTAATCTGA AAATAGCAAC CCAGAATGTA AAAAGAAAA AACTGGGGGG AAAAAGACCA   1000
GGTCTACAGT GATAGAGCAA AGCATCAAAG AATCTTTAAG GGAGGTTTAA AAAAAAAAA   1060
AAAAAAAAAG ATTGGTTGCC TCTGCCTTTG TGATCCTGAG TCCAGAATGG TACACAATGT   1120
GATTTTATGG TGATGTCACT CACCTAGACA ACCAGAGGCT GGCATTGAGG CTAACCTCCA   1180
ACACAGTGCA TCTCAGATGC CTCAGTAGGC ATCAGTATGT CACTCTGGTC CCTTTAAAGA   1240
GCAATCCTGG AAGAAGCAGG AGGGAGGGTG GCTTGCTGT TGTTGGGACA TGGCAATCTA   1300
GACCGGTAGC AGCGCCTCGC TGACAGCTTG GGAGGAAACC TGAGATCTGT GTTTTTAAA   1360
TTGATCGTTC TTCATGGGGG TAAGAAAAGC TGGTCTGGAG TTGCTGAATG TTGCATTAAT   1420
TGTGCTGTTT GCTTGTAGTT GAATCCC                                      1447
```

( 2 ) INFORMATION FOR SEQ ID NO:15:

( i ) SEQUENCE CHARACTERISTICS:
       ( A ) LENGTH: 187 amino acids
       ( B ) TYPE: amino acid
       ( D ) TOPOLOGY: linear ( i i ) MOLECULE TYPE: protein ( x i ) SEQUENCE DESCRIPTION: SEQ ID NO:15:

```
Met Pro Val Asp Leu Ser Lys Trp Ser Gly Pro Leu Ser Leu Gln Glu
 1               5                  10                  15

Val Asp Glu Gln Pro Gln His Pro Leu His Val Thr Tyr Ala Gly Ala
                20                  25                  30

Ala Val Asp Glu Leu Gly Lys Val Leu Thr Pro Thr Gln Val Lys Asn
            35                  40                  45

Arg Pro Thr Ser Ile Ser Trp Asp Gly Leu Asp Ser Gly Lys Leu Tyr
    50                  55                  60

Thr Leu Val Leu Thr Asp Pro Asp Ala Pro Ser Arg Lys Asp Pro Lys
65                  70                  75                  80

Tyr Arg Glu Trp His His Phe Leu Val Val Asn Met Lys Gly Asn Asp
```

|     |     |     |     | 85  |     |     |     |     | 90  |     |     |     |     | 95  |     |     |
| --- | --- | --- | --- | --- | --- | --- | --- | --- | --- | --- | --- | --- | --- | --- | --- | --- |
| Ile | Ser | Ser | Gly<br>100 | Thr | Val | Leu | Ser | Asp<br>105 | Tyr | Val | Gly | Ser | Gly<br>110 | Pro | Pro |

Lys Gly Thr Gly Leu His Arg Tyr Val Trp Leu Val Tyr Glu Gln Asp
         115             120                 125

Arg Pro Leu Lys Cys Asp Glu Pro Ile Leu Ser Asn Arg Ser Gly Asp
    130             135                 140

His Arg Gly Lys Phe Lys Val Ala Ser Phe Arg Lys Lys Tyr Glu Leu
145             150             155                         160

Arg Ala Pro Val Ala Gly Thr Cys Tyr Gln Ala Glu Trp Asp Asp Tyr
              165             170                 175

Val Pro Lys Leu Tyr Glu Gln Leu Ser Gly Lys
              180             185

( 2 ) INFORMATION FOR SEQ ID NO:16:

( i ) SEQUENCE CHARACTERISTICS:
        ( A ) LENGTH: 33 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
        ( A ) ORGANISM: homo sapiens
        ( F ) TISSUE TYPE: placental tissue ( v i i ) IMMEDIATE SOURCE:
        ( B ) CLONE: p1-3

( i x ) FEATURE:
        ( A ) NAME/KEY: CDS
        ( B ) LOCATION: 1..33

( x i ) SEQUENCE DESCRIPTION: SEQ ID NO:16:

CCG GTG GAC CTC AGC AAG TGG TCC GGG CCC TTG                                   33
Pro Val Asp Leu Ser Lys Trp Ser Gly Pro Leu
 1           5                   10

( 2 ) INFORMATION FOR SEQ ID NO:17:

( i ) SEQUENCE CHARACTERISTICS:
        ( A ) LENGTH: 11 amino acids
        ( B ) TYPE: amino acid
        ( D ) TOPOLOGY: linear ( i i ) MOLECULE TYPE: protein ( v i ) ORIGINAL SOURCE:
        ( A ) ORGANISM: homo sapiens
        ( F ) TISSUE TYPE: placental tissue ( i x ) FEATURE:
        ( A ) NAME/KEY: Peptide
        ( B ) LOCATION: 1..11

( x i ) SEQUENCE DESCRIPTION: SEQ ID NO:17:

Pro Val Asp Leu Ser Lys Trp Ser Gly Pro Leu
 1           5                   10

( 2 ) INFORMATION FOR SEQ ID NO:18:

( i ) SEQUENCE CHARACTERISTICS:
        ( A ) LENGTH: 6 amino acids (B) TYPE: amino acid
(D) TOPOLOGY: linear (ii) MOLECULE TYPE: peptide (xi) SEQUENCE DESCRIPTION: SEQ ID NO:18:

```
Val  Asp  Leu  Ser  Lys  Trp
 1                 5
```

(2) INFORMATION FOR SEQ ID NO:19:

(i) SEQUENCE CHARACTERISTICS:
      (A) LENGTH: 5 amino acids
      (B) TYPE: amino acid
      (D) TOPOLOGY: linear (ii) MOLECULE TYPE: peptide (xi) SEQUENCE DESCRIPTION: SEQ ID NO:19:

```
Leu  Ser  Lys  Trp  Ser
 1                 5
```

(2) INFORMATION FOR SEQ ID NO:20:

(i) SEQUENCE CHARACTERISTICS:
      (A) LENGTH: 6 amino acids
      (B) TYPE: amino acid
      (D) TOPOLOGY: linear (ii) MOLECULE TYPE: peptide (xi) SEQUENCE DESCRIPTION: SEQ ID NO:20:

```
Lys  Trp  Ser  Gly  Pro  Leu
 1                 5
```

(2) INFORMATION FOR SEQ ID NO:21:

(i) SEQUENCE CHARACTERISTICS:
      (A) LENGTH: 11 amino acids
      (B) TYPE: amino acid
      (D) TOPOLOGY: linear (ii) MOLECULE TYPE: peptide (xi) SEQUENCE DESCRIPTION: SEQ ID NO:21:

```
Pro  Val  Asp  Leu  Ser  Lys  Trp  Ser  Gly  Pro  Leu
 1                 5                          10
```

(2) INFORMATION FOR SEQ ID NO:22:

(i) SEQUENCE CHARACTERISTICS:
      (A) LENGTH: 10 amino acids
      (B) TYPE: amino acid
      (D) TOPOLOGY: linear (ii) MOLECULE TYPE: peptide (xi) SEQUENCE DESCRIPTION: SEQ ID NO:22:

```
Val  Asp  Leu  Ser  Lys  Trp  Ser  Gly  Pro  Leu
 1                 5                       10
```

(2) INFORMATION FOR SEQ ID NO:23:

(i) SEQUENCE CHARACTERISTICS:
      (A) LENGTH: 9 amino acids
      (B) TYPE: amino acid
      (D) TOPOLOGY: linear (ii) MOLECULE TYPE: peptide ( x i ) SEQUENCE DESCRIPTION: SEQ ID NO:23:

```
Asp Leu Ser Lys Trp Ser Gly Pro Leu
1               5
```

( 2 ) INFORMATION FOR SEQ ID NO:24:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:24:

```
Leu Ser Lys Trp Ser Gly Pro Leu
1           5
```

( 2 ) INFORMATION FOR SEQ ID NO:25:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:25:

```
Ser Lys Trp Ser Gly Pro Leu
1           5
```